United States Patent
Custer et al.

(10) Patent No.: US 7,066,884 B2
(45) Date of Patent: Jun. 27, 2006

(54) SYSTEM, METHOD, AND DEVICE FOR NON-INVASIVE BODY FLUID SAMPLING AND ANALYSIS

(75) Inventors: Linda Custer, Marlborough, MA (US); Tuan A. Elstrom, Lake Bluff, IL (US); Scott C. Kellogg, Boston, MA (US); Joseph Kost, Cambridge, MA (US); Nicholas F. Warner, Belmont, MA (US)

(73) Assignee: Sontra Medical, Inc., Cambridge, MA (US)

( * ) Notice: Subject to any disclaimer, the term of this patent is extended or adjusted under 35 U.S.C. 154(b) by 311 days.

(21) Appl. No.: 09/979,096

(22) PCT Filed: Mar. 16, 2001

(86) PCT No.: PCT/US01/08489

§ 371 (c)(1), (2), (4) Date: Mar. 11, 2002

(87) PCT Pub. No.: WO01/70330

PCT Pub. Date: Sep. 27, 2001

(65) Prior Publication Data

US 2003/0100846 A1 May 29, 2003

Related U.S. Application Data

(60) Provisional application No. 60/189,971, filed on Mar. 17, 2000.

(51) Int. Cl.
*A61B 5/00* (2006.01)

(52) U.S. Cl. .................. 600/309; 600/573
(58) Field of Classification Search ............ 600/309, 600/310, 311, 345, 347, 348, 362, 365, 573, 600/584
See application file for complete search history.

(56) References Cited

U.S. PATENT DOCUMENTS 3,551,554 A 12/1970 Herschler et al.

(Continued)

FOREIGN PATENT DOCUMENTS

AU 706662 2/1997

(Continued)

OTHER PUBLICATIONS

Apfel, R.E., et al., "Possibility of Microcavitation from Diagnostic Ultrasound," IEEE Transactions on Ultrasonics, Ferroelectrics, and Frequency Control, vol. 33, No. 2, pp. 139–142 (Mar., 1986).

(Continued)

*Primary Examiner*—Eric F. Winakur
(74) *Attorney, Agent, or Firm*—Hunton & Williams LLP

(57) ABSTRACT

A system, method, and device for non-invasive body fluid sampling is provided. According to one embodiment of the present invention, the system includes a controller that controls the generation of ultrasound; an ultrasonic applicator that applies the ultrasound to an area of biological membrane; a receiver that contacts the area of biological membrane and receives body fluid through and out of the area of biological membrane; and a meter that interacts with the receiver and detects the presence of at least one analyte in the body fluid in the receiver. The receiver may include a membrane and a medium, such as a hydrogel, a fluid, or a liquid, that is contained in the membrane. According to one embodiment of the present invention, the method includes the steps of (1) identifying an area of biological membrane having a permeability level; (2) increasing the permeability level of the area of biological membrane; (3) contacting the area of biological membrane with a receiver; (4) extracting body fluid through and out of the area of biological membrane; (5) providing an external force to enhance the body fluid extraction; (6) collecting the body fluid in the receiver; (7) analyzing the collected body fluid for the presence of at least one analyte; and (8) providing the results of the step of analyzing the body fluid.

68 Claims, 6 Drawing Sheets

U.S. PATENT DOCUMENTS

| | | |
|---|---|---|
| 3,711,602 A | 1/1973 | Herschler |
| 3,711,606 A | 1/1973 | Herschler |
| 3,828,769 A | 8/1974 | Mettler |
| 4,002,221 A | 1/1977 | Buchalter |
| 4,020,830 A | 5/1977 | Johnson et al. |
| 4,127,125 A | 11/1978 | Takemoto et al. |
| 4,144,317 A | 3/1979 | Higuchi et al. |
| 4,144,646 A | 3/1979 | Takemoto et al. |
| 4,176,664 A | 12/1979 | Kalish |
| 4,249,531 A | 2/1981 | Heller et al. |
| 4,280,494 A | 7/1981 | Cosgrove, Jr. et al. |
| 4,309,989 A | 1/1982 | Fahim |
| 4,372,296 A | 2/1983 | Fahim |
| 4,457,748 A | 7/1984 | Lattin |
| 4,537,776 A | 8/1985 | Cooper |
| 4,557,943 A | 12/1985 | Rosler et al. |
| 4,563,184 A | 1/1986 | Korol |
| 4,595,011 A | 6/1986 | Phillips |
| 4,646,725 A | 3/1987 | Moasser |
| 4,657,543 A | 4/1987 | Langer et al. |
| 4,683,242 A | 7/1987 | Poser |
| 4,698,058 A | 10/1987 | Greenfeld et al. |
| 4,702,732 A | 10/1987 | Powers et al. |
| 4,732,153 A | 3/1988 | Phillips |
| 4,767,402 A | 8/1988 | Kost et al. |
| 4,779,806 A | 10/1988 | Langer et al. |
| 4,780,212 A | 10/1988 | Kost et al. |
| 4,786,277 A | 11/1988 | Powers |
| 4,787,070 A | 11/1988 | Suzuki et al. |
| 4,787,888 A | 11/1988 | Fox |
| 4,820,720 A | 4/1989 | Sanders et al. |
| 4,821,733 A | 4/1989 | Peck |
| 4,821,740 A | 4/1989 | Tachibana et al. |
| 4,834,978 A | 5/1989 | Nuwayser |
| 4,855,298 A | 8/1989 | Yamada et al. |
| 4,860,058 A | 8/1989 | Kobayashi et al. |
| 4,863,970 A | 9/1989 | Patel et al. |
| 4,866,050 A | 9/1989 | Ben-Amoz |
| 4,933,062 A | 6/1990 | Shaw et al. |
| 4,948,587 A | 8/1990 | Kost et al. |
| 4,953,552 A | 9/1990 | DeMarzo |
| 4,953,565 A | 9/1990 | Tachibana et al. |
| 4,970,145 A | 11/1990 | Bennetto et al. |
| 4,981,779 A | 1/1991 | Wagner |
| 4,986,271 A | 1/1991 | Wilkins |
| 5,001,051 A | 3/1991 | Miller et al. |
| 5,006,342 A | 4/1991 | Cleary et al. |
| 5,007,438 A | 4/1991 | Tachibana et al. |
| 5,016,615 A | 5/1991 | Driller et al. |
| 5,019,034 A | 5/1991 | Weaver et al. |
| 5,036,861 A | 8/1991 | Sembrowich et al. |
| 5,050,604 A | 9/1991 | Reshef et al. |
| 5,069,908 A | 12/1991 | Henley |
| 5,076,273 A | 12/1991 | Schoendorfer et al. |
| 5,078,144 A | 1/1992 | Sekino et al. |
| 5,082,786 A | 1/1992 | Nakamoto |
| 5,086,229 A | 2/1992 | Rosenthal et al. |
| 5,115,805 A | 5/1992 | Bommannan et al. |
| 5,118,404 A | 6/1992 | Saito |
| 5,119,819 A | 6/1992 | Thomas et al. |
| 5,120,544 A | 6/1992 | Henley |
| 5,134,057 A | 7/1992 | Kuypers et al. |
| 5,135,753 A | 8/1992 | Baker et al. |
| 5,139,023 A | 8/1992 | Stanley et al. |
| 5,140,985 A | 8/1992 | Schroeder et al. |
| 5,161,532 A | 11/1992 | Joseph |
| 5,165,407 A | 11/1992 | Wilson et al. |
| 5,165,418 A | 11/1992 | Tankovich |
| 5,171,215 A | 12/1992 | Flanagan |
| 5,197,946 A | 3/1993 | Tachibana |
| 5,215,520 A | 6/1993 | Shroot et al. |
| 5,215,887 A | 6/1993 | Saito |
| 5,230,334 A | 7/1993 | Klopotek |
| 5,231,975 A | 8/1993 | Bommannan et al. |
| 5,236,410 A | 8/1993 | Granov et al. |
| 5,250,419 A | 10/1993 | Bernard et al. |
| 5,267,985 A | 12/1993 | Shimada et al. |
| 5,279,543 A | 1/1994 | Glikfeld et al. |
| 5,282,785 A | 2/1994 | Shapland et al. |
| 5,286,254 A | 2/1994 | Shapland et al. |
| 5,315,998 A | 5/1994 | Tachibana et al. |
| 5,323,769 A | 6/1994 | Bommannan et al. |
| 5,330,756 A | 7/1994 | Steuart et al. |
| 5,362,307 A | 11/1994 | Guy et al. |
| 5,364,838 A | 11/1994 | Rubsamen |
| 5,386,837 A | 2/1995 | Sterzer |
| 5,401,237 A | 3/1995 | Tachibana et al. |
| 5,405,366 A | 4/1995 | Fox et al. |
| 5,405,614 A | 4/1995 | D'Angelo et al. |
| 5,413,550 A | 5/1995 | Castel |
| 5,415,629 A | 5/1995 | Henley |
| 5,421,816 A | 6/1995 | Lipkovker |
| 5,429,735 A | 7/1995 | Johnson et al. |
| 5,443,080 A | 8/1995 | D'Angelo et al. |
| 5,445,611 A | 8/1995 | Eppstein et al. |
| 5,458,140 A | 10/1995 | Eppstein et al. |
| 5,470,582 A | 11/1995 | Supersaxo et al. |
| 5,534,496 A | 7/1996 | Lee et al. |
| 5,538,503 A | 7/1996 | Henley |
| 5,569,198 A | 10/1996 | Racchini |
| 5,573,778 A | 11/1996 | Therriault et al. |
| 5,582,184 A | 12/1996 | Erickson et al. |
| 5,582,586 A | 12/1996 | Tachibana et al. |
| 5,617,851 A | 4/1997 | Lipkovker |
| 5,618,275 A | 4/1997 | Bock |
| 5,626,554 A | 5/1997 | Ryaby et al. |
| 5,636,632 A | 6/1997 | Bommannan et al. |
| 5,646,221 A | 7/1997 | Inagi et al. |
| 5,655,539 A | 8/1997 | Wang et al. |
| 5,656,016 A | 8/1997 | Ogden |
| 5,658,247 A | 8/1997 | Henley |
| 5,667,487 A | 9/1997 | Henley |
| 5,722,397 A | 3/1998 | Eppstein |
| 5,730,714 A | 3/1998 | Guy et al. |
| 5,735,273 A | 4/1998 | Kurnik et al. |
| 5,746,217 A | 5/1998 | Erickson et al. |
| 5,771,890 A | 6/1998 | Tamada |
| 5,814,599 A | 9/1998 | Mitragotri et al. |
| 5,820,570 A | 10/1998 | Erickson et al. |
| 5,827,183 A | 10/1998 | Kurnik et al. |
| 5,851,438 A | 12/1998 | Chan |
| 5,885,211 A | 3/1999 | Eppstein et al. |
| 5,902,603 A | 5/1999 | Chen et al. |
| 5,906,830 A | 5/1999 | Farinas et al. |
| 5,947,921 A | 9/1999 | Johnson et al. |
| 5,961,451 A | 10/1999 | Reber et al. |
| 5,989,409 A | 11/1999 | Kurnik et al. |
| 6,002,961 A | 12/1999 | Mitragotri et al. |
| 6,009,343 A | 12/1999 | Shain et al. |
| 6,018,678 A | 1/2000 | Mitragotri et al. |
| 6,041,253 A | 3/2000 | Kost et al. |
| 6,190,315 B1 | 2/2001 | Kost et al. |
| 6,234,990 B1 * | 5/2001 | Rowe et al. .................. 604/22 |
| 6,251,083 B1 * | 6/2001 | Yum et al. .................. 600/584 |
| 6,283,926 B1 | 9/2001 | Cunningham et al. |
| 6,299,578 B1 | 10/2001 | Kurnik et al. |
| 6,309,351 B1 | 10/2001 | Kurnik et al. |
| 6,468,229 B1 | 10/2002 | Grace et al. |
| 6,482,604 B1 | 11/2002 | Kwon |
| 6,487,447 B1 | 11/2002 | Weimann et al. |
| 6,491,657 B1 | 12/2002 | Rowe et al. |

| | | | |
|---|---|---|---|
| 6,503,198 B1 | 1/2003 | Aronowtiz et al. | |
| 6,535,753 B1 | 3/2003 | Raskas | |
| 6,540,675 B1 | 4/2003 | Aceti et al. | |
| 2004/0039418 A1 | 2/2004 | Elstrom et al. | |
| 2004/0171980 A1 | 9/2004 | Mitragotri et al. | |

FOREIGN PATENT DOCUMENTS

| | | |
|---|---|---|
| CA | 2196746 | 8/1991 |
| CA | 1324051 | 11/1993 |
| CA | 2167393 | 1/1995 |
| CA | 2226176 | 1/1997 |
| CA | 2229480 | 3/1997 |
| CA | 2212826 | 7/1997 |
| CA | 2075624 | 11/1997 |
| DE | 0 245 535 | 11/1987 |
| EP | DE 2756460 | 6/1979 |
| EP | 0043738 | 1/1982 |
| EP | 0 245 535 | 11/1987 |
| EP | 0 246 341 | 11/1987 |
| EP | 0 247 850 | 12/1987 |
| EP | 0 278 074 | 8/1988 |
| EP | 0 304 304 | 2/1989 |
| EP | 0 368 408 | 5/1990 |
| EP | 0386408 | 9/1990 |
| EP | 0 453 283 | 10/1991 |
| EP | 0495531 | 7/1992 |
| EP | 0 513 789 | 11/1992 |
| EP | 0612525 | 8/1994 |
| EP | 0 625 360 | 11/1994 |
| EP | 0 649 628 | 4/1995 |
| EP | 0 736 305 | 10/1996 |
| EP | 0847775 A1 | 6/1998 |
| GB | 1577551 | 10/1980 |
| GB | 2153223 | 8/1985 |
| JP | 59095060 | 5/1984 |
| JP | 62133937 | 6/1987 |
| JP | 3170172 | 7/1991 |
| SU | 445433 | 11/1974 |
| SU | 556805 | 5/1977 |
| SU | 591186 | 2/1978 |
| SU | 506421 | 3/1978 |
| SU | 910157 | 3/1982 |
| WO | WO 87/07295 | 12/1987 |
| WO | WO 8800001 | 1/1988 |
| WO | WO 9001971 | 3/1990 |
| WO | WO 9015568 | 12/1990 |
| WO | WO 9112772 | 9/1991 |
| WO | WO 94/05368 | 8/1992 |
| WO | WO 92/14449 | 9/1992 |
| WO | WO 93/05096 | 3/1993 |
| WO | WO 9320745 | 10/1993 |
| WO | WO 9408655 | 4/1994 |
| WO | WO 95/02357 | 1/1995 |
| WO | WO 96/00110 | 1/1996 |
| WO | WO 97/02811 | 1/1997 |
| WO | WO 9704832 | 2/1997 |
| WO | WO 97/04832 | 2/1997 |
| WO | WO 97/10499 | 3/1997 |
| WO | WO 97/13548 | 4/1997 |
| WO | WO 97/18851 | 5/1997 |
| WO | WO 97/24059 | 7/1997 |
| WO | WO 97/30628 | 8/1997 |
| WO | WO 97/30749 | 8/1997 |
| WO | WO 98/00194 | 1/1998 |
| WO | WO 98/17184 | 4/1998 |
| WO | WO 98/20331 | 5/1998 |
| WO | WO 98/28037 | 7/1998 |
| WO | WO 98/34541 | 8/1998 |
| WO | WO 98/42252 | 10/1998 |
| WO | WO 99/34857 | 7/1999 |
| WO | WO 99/34858 | 7/1999 |
| WO | WO 00/04821 | 2/2000 |
| WO | WO 00/35351 | 6/2000 |
| WO | WO 00/35357 | 6/2000 |
| WO | WO 01/70330 | 9/2001 |
| WO | WO 92/13567 | 8/2002 |

OTHER PUBLICATIONS

Aungst, B. J. et al., "Contributions of Drug Solubilization, Partitioning, Barrier Disruption, and Solvent Permeation to the Enhancement of Skin Permeation of Various Compounds with Fatty Acids," Pharmaceutical Research. vol. 7, No. 7, pp. 712–718 (Jul., 1990).

Barry, E. W., "Mode of Action of Penetration Enhancers in Human Skin," Journal of Controlled Release, vol. 6, pp. 85–97 (1987).

Bommer, Jurgen, Subutaneous Erythropoietin, The Lancet, vol. II, No. 8607 (Aug. 13, 1988).

Burnett, R. R., "Iontophoresis," Transdermal Drug Delivery, pp. 247–291 (1989).

Cleary, G.W., "Transdermal Controlled Release Systems," Medical Applications of Controlled Release, vol. 1, pp. 203–251 (1984).

Clegg, R. M., et al., "Translational diffusion of proteins and lipids in artifical lipid bilayer, membranes. A comparison of Experiment with Theory," Progress in Protein–Lipid Interactions, vol. 1, pp. 172–229 (1985).

D'Emanuele, A., et al., "An Investigation of the Effects of Ultrasound on Degradable Polyanhydride Matrices," Macromolecular, vol. 25, No. 25, pp. 511–515 (1992).

Davis, J. M., et al., "Characterization of Recombinant Human Erythropoietin Produced in Chinese Hamster Ovary Cells," Biochemistry, vol. 26, No. 9, pp. 2633–2638 (1987).

Ebert, C. D., et al., "Transbuccal Absorption of Diclofenac Sodium in a Dog Model," pp. 310–321 (1987).

Eggerth, R. M., et al., "Evaluation of Hamster Cheek Pouch as a Model for Buccal Absorption," Proceed. Intern.Symp. Control. Rel. Bioact. Mater., vol. 14, pp. 180–181 (1987).

Elias, J. J., "The Microscopic Structure of the Epidermis and Its Derivatives," Percutaneous Absorption Mechanisms Methodology Drug Delivery, pp. 3–12 (1989).

Flynn, G. L., "Mechanism of Percutaneous Absorption from Physicochemical Evidence," Percutaneous Absorption Mechanisms Methodology Drug Delivery, pp. 27–51 (1989).

Friedman, R., M., Interferons A Primer, ISBN 0–12–268280–7.

Gaertner, W., "Frequency Dependence of Ultrasonic Cavitation," The Journal of the Acoustical Society of America, vol. 26, No. 6, pp. 977–980 (Nov., 1954).

Ghanem, A, et al., "The effects of ethanol on the transport of lipophilic and polar permeants across hairless mouse skin: Methods/validation of a novel approach," International Journal of Pharmaceutics, vol. 78, pp. 137–220 (1992).

Grups, J. W.,et al., "Cyclic Interferon Gamma Treatment of Patients with Metastatic Renal Carcinoma," British Journal of Urology, vol. 64, No. 44, pp. 218–220 (1989).

Hansch, C., et al., Substituent Constants for Correlation Analysis in Chemistry and Biology (1979).

Junginger, H.E., et al., "Visualization of Drug Transport Across Human Skin and the Influence of Penetration Enhancers," Drug Permeation Enhancement Theory and Applications, pp. 59–89 (1994).

Kasting, G.B., et al., "Prodrugs for Dermal Delivery: Solubility, Molecular Size, and Functional Group Effects," Prodrugs Topical and Ocular Drug Delivery, pp. 116–161 (1992).

Kost, J., et al., "Ultrasound–Mediated Transedermal Drug Delivery", Topical Drug Bioacailability, Bioequivalence, and Penetration, pp. 91–104 (1993).

Kost, J., et al., "Ultrasound Effect on Transdermal Drug Delivery," Ben Gurion University, Dept. of Chem. Engineering, Beer Sheva Israel MIT, Dept. of Applied Biological Sciences.

Krall, L.P., World Book of Diabetes in Practice, vol. 3, pp. 2–7 (1988).

Lee, V. H. L., et al., "Nasal Peptide and Protein Absorption Promotors: Aminopeptidase Inhibition as a Predictor of Absorption Enhancement Potency of Bile Salts," Proceed. Intern. Symp. Control, Rel. Bioact. Mater, vol. 14, pp. 53–54 (1987).

Lee, V. H. L., et al., Protease Inhibition as an Additional Mechanism for the Nasal Absorption Enhancement Effect of Sodium Taurodihydrofusidate, Proceed, Intern, Symp. Control. Rel. Bioact. Mater vol. 14, No.83, pp. 55–56 (1987).

Levy, D., et al., "Effect of Ultrasound on Transdermal Drug Delivery to Rats and Guinea Pigs," J. Clin Invest., vol. 83, No. 6, 2074–2078 (Jun., 1989).

Liu, P., et al., "Cotransport of Estradiol and Ethanol Through Human Skin in Vitro: Understanding the Permeant/Enhancer Flux Relationship," Pharmaceutical Research, vol. 8, No. 7, pp. 938–944 (Jul., 1991).

Liu, L. S., et al., "Experimental Approach to Elucidate the Mechanism of Ultrasound–Enhanced Polymer Erosion and Release of Incorporated Substances," Macromolecules, vol. 25, pp. 123–128 (1992).

Machluf, M., et al., "Ultrasonically enhanced transdermal drug delivery. Experimental Approaches to Eludidate the Mechanism," J. Biomater. Sci. Polymer Edn., vol. 5, No. 1/2, pp. 147–156 (1993).

Mak, V. H., et al., "Oleic Acid Concentration and Effect in Human Stratum Corneum: Non–Invasive Determination by Attenuated Total Reflectance Infrared Spectroscopy in Vivo," Journal of Controlled Release, vol. 12, pp. 67–75 (1990).

Mitragotri, S., et al., "Ultrasound–Mediated Transdermal Protein Delivery," Science , vol. 269, 850–852 (Aug. 11, 1995).

Mitragotri, S., et al., "A Mechanistic Study of Ultrasonically–Enhanced Transdermal Drug Delivery," Journal of Pharmaceutical Sciences, vol. 84, No. 6, pp. 697–706 (Jun., 1995).

Morimoto, Y., et al., "Predition of Skin Permeability of Drugs: Comparison of Human and Hairless Rat Skin," J. Pharm. Pharmacol, vol. 44, No. 8, pp. 634–639 (Aug. 8, 1992).

Nagai, T., et al., "Buccal/Gingival Drug Delivery Systems," Journal of Controlled Release, vol. 6, pp. 353–360 (1987).

Newman, J., et al., "Hydrocortisone Phonophoresis," Journal of the American Podiatric Medical Association, vol. 82, No. 8, pp. 432–435 (Aug. 8, 1992).

Olanoff, L., et al., "Method to Enhance Intranasal Peptide Delivery," Controlled Release Technology, 302–309 (1987).

Ongpipattanakul, B., et al., "Evidence that Oleic Acid Exists in a Separate Phase Within Stratum Corneum Lipids," Pharmaceutical Research, vol. 8, No. 3, pp. 350–354 (Mar. 3, 1991).

Parkin, J. M., et al., "Atopic Manifestations in the Acquired Immune Deficiency Syndrome: Response to Recombinant Interferon Gamma," British Medical Journal, vol. 294, pp. 1185–1186 (May 2, 1987).

Perry, R., Perry's Chemical Engineers' Handbook, $6^{th}$ Edition.

Pishko, M., et al., "Amperometric Glucose Microelectrodes Prepared through Immobilization of Glucose Oxidase in Redox Hydrogels," Anal. Chem., vol. 63, pp. 2268–2272 (1991).

Potts, R. O., et al., "Predicting Skin Permeability," Pharmaceutical Research, vol. 9, No. 5, pp. 663–669 (May, 1992)

Prausnitz, M. R., et al., "Electroporation of Mammalian Skin: A Mechanism to Enhance Transdermal Drug Delivery," Proc. Natl. Acad. Sci. USA, vol. 90, No. 22, pp. 10504–10508 (Nov. 15, 1993).

Quillen, W. S., "Phonophoresis: A Review of the Literature and Technique," Athletic Training, vol. 15, pp. 109–110 (Summer, 1980).

Robinson, et al., "Influence of Drug Properties on Design," Controlled Drug Delivery, pp. 42–43.

Rosell, J., et al., "Skin Impedance From 1HZ to 1MHz," IEEE Trans. Biomed. Eng. vol. 35, No. 8, 649–651 (Aug. 8, 1988).

Skauen, D. M., et al., "Phonophoresis," Int. J. Pharm., vol. 20, No. 3, 265–245 (Jul., 1984).

Stringfellow, D. A., Clinical Application of Interferons and Their Inducers, $2^{nd}$ Edition (1986).

Tamada, J. A., et al., "Correlation of Blood Glucose with Inotophoretic Glucose Flux in Human Subjects for Glucose Monitoring," Proceedings of the $22^{nd}$ International Symposiuim on Controlled Release of Bioactive Materials, vol. 22, pp. 129–130 (1995).

Tocanne, J.F., et al., "Lipid Lateral Diffusion and Membrane Organization," FEBS Letters, vol. 257, pp. 10–16 (1989).

Tyle, Praveen, et al., "Drug Delivery by Phonophoresis," Pharmaceutical Research, vol. 6, pp. 355–361 (1989).

Walker, M., et al., "Oleic acid—a membrane fluidiser or fluid within the membrane?,"International Journal of Pharmaceutics, vol. 71, R–1–R–4 (1991).

Walmsley, A. D., "Applications of Ultrasound in Dentistry," Ultrasound in medicine and biology, vol. 14, pp. 7–14 (1988).

Walters, K. A., "Penetration Enhancers and Their Use in Transdermal Therapeutic Systems," Transdermal Drug Delivery, vol. 35, 197–246 (1989).

Wester, R. C., et al., "Animal Models for Percutaneous Absorption," Topical Drug Bioavailability Bioequivalence, and Penetration, pp. 333–349 (1993).

Wheatley, M. A., et al., "Use of Ussing Chamber for Investigation of Drug Delivery Across Viable Nasal Tissue Membranes," Proceed. Intern. Symp. Control. Rel. Bioact. Mater. (Controlled Release Society, Inc. vol. 14, pp. 26–27 (1987).

Williams, A.C., et al., "On the non–Gaussian distribution of human skin permeabilities," International Journal of Pharmaeceutics, vol. 86, pp. 69–77 (1992).

Wilscut, A., et al., "Estimating Skin Permeation. The Validation of Five Mathematical Skin Permeation Models," Chemosphere, vol. 30, pp. 1275–1296 (1995).

U.S. Appl. No 09/868,442, Mitragotri et al., dated Dec. 17, 1999.

U.S. Appl. No. 10/792,862, Mitragotri et al., dated Mar. 5, 2004.

A. Boucaud et al., "In vitro study of low–frequency ultrasound–enhanced transdermal transport of fentanyl and caffeine across human and hairless rat skin," International J. Pharmaceuticals, vol. 228, Nos. 1–2, pp. 69–77 (Oct. 2001).
Philip S. Burton et al., "Metabolism and Transport of Peptide Across Intestinal Mucosa," 14 Proceed. Intern. Symp. Control. Rel. Bioact. Mater 6 (Controlled Release Society, Inc. 1987).
Etienne Camel, "Ultrasound," Percutaneous Penetration Enhancers 369–382 (Eric W. Smith et al. eds. 1995).
Egorov, E.A. et al., "Use of the Variants of the Pharmacophysical Influence in Ophthalmology," 102 Ophthalmology Journal #2 (1992).
A.D. Keith and W. Snipes, "Polymeric Carriers for Active Agents," Transdermal and Related Drug Delivery Systems pp. 223–279 (D.A. Jones ed. 1984).
Joseph Kost et al., "Synergistic Effect of Electric Field and Ultrasound on Transdermal Transport," Pharmaceutical Research, vol. 13, No. 4, pp. 633–638 (1996).
Samir Mitragotri et al., "Sonophoresis: Enhanced Transdermal Drug Delivery by Application of Ultrasound," 14 Encyclopedia of Pharmaceutical Technology 103–122 (1996).
S. Mitragotri, "Synergistic Effect of Enhancers for Transdermal Drug Delivery," Pharm Res. vol. 17, No. 11, pp. 1354–1359 (2000).
S. Mitragotri and Joseph Kost, "Transdermal Delivery of Heparin and Low–Molecular Weight Heparin Using Low–Frequency Ultrasound," Pharmaceutical Reserach, vol. 18, No. 8, pp. 1151–1156 (Aug. 2001).
D. Monti et al., "Comparison of the effect of ultrasound of chemical enhancers of transdermal permeation of caffeine and morphine through hairless mouse skin in vitro," International J. Pharmaceuticals, vol. 229, Nos. 1–2, pp. 131–137 (Oct. 2001).
Veillard et al., "Buccal Controlled Delivery of Peptides," Proceed. Intern. Symp. Control. Rel. Bioact. Mater (Controlled Release Society, Inc.) 14:6 (1987).
Agrawl, C.M. et al., "The effects of ultrasound irradiation on a biodegradable 50–50% copolymer of polylactic and polylactic and polyglycolic acids,"28 Journal of Biomedical Materials Research 851–859 (1994).
G.W. Albin et al., "Theoretical and Experimental Studies of Glucose Sensitive Membranes, "6 Journal of Controlled Release 267–291 (1987).
Allcock, H., et al., "Activity of Urea Amidohydrolase Immobilized within Polydi(methoxy–ethoxyethoxy-)phosphazene Hydrogels,"Biomaterials, vol. 15, No. 7, pp. 502–506 (Jun. 1994).
Asakura et al. "Immobilization of Glucose Oxidase on Nonwoven Fabrics with Bombyx mori Silk Fibroin Gel," Journal of Applied Polymer Science, vol. 46, No. 1, pp. 49–53 (Sep. 5, 1992).
Bhat, et al., "Optimization on delivery of betamethasone-–dipropionate from skin preparation," Indian Drugs 32:211–14 (1995).
Blackshear, "Implantable Drug–Delivery Systems," Scientific America, pp. 66–73 (604193) (Dec. 1979).
Domb et al., "Polyanhydrides–Sysnthesis and Characterization," 107 Advances in Polymer Science: 93–141 (1993).
Eppstein, D.A. et al., "Alternative Delivery Systems for Peptides and Proteins as Drugs," 5 CRC Reviews in Therapeutic Drug Carrier Systems 99–139 (1988).
Eppstein, D.A. et al., "Applications of Liposome Formulations for Antimicrobial/Antiviral Therapy," Liposomes as Drug Carriers 311–323 (John Wiley & Sons 1988).

Eppstein, D.A. et al., "Medical Utility of Inteferons: Approaches to Increasing Therapeutic Efficacy" 7 Pharmacy International 195–199 (1986).
Heller, J., et al. "Controlled Drug Release by Polymer Dissolution II Enzyme–Mediated Delivery Device," Journal of Pharmaceutical Sciences, vol. 68, No. 7, pp. 919–921 (Jul. 1979).
I.A. Murav'ev, et al., "Mechanism of the Release of Pharmaceutical Substances from Ointment Bases by Ultrasound," Chemical Abstracts, vol. 84, No. 4, p. 333, Abstract No. 22054g (Jan. 26, 1996).
Mark E. Johnson et al., "Synergistic Effects of Chemical Enhancers and Therapeutic Ultrasound on Transdermal Drug Delivery," 85 J. Pharmaceutical Sciences 670–670 (Jul. 1996).
Kamath, et al., "Biodegradable hydrogels in Drug Delivery," 11 Advanced Drug Delivery Reviews 59–84 (1993).
Kost, J., et al., "Glucose–Sensitive Membranes Containing Glucose Oxidase: Activity, Swelling, and Permeability Studies," Journal of Biomedical Materials Reserach, vol. 19, pp. 1117–1133 (1985).
Langer et al., "Chemical and Physical Structure of Polymers as Carriers for Controlled Release of Bioactive Agents: A Review," Journal of Macromolecular Science, Reviews on Macromolecular Chemistry and Physics, C23(1), 61–126 (1983).
Lesho et al., "A Photopatterened Glucose Responsive Hydrogel for Use in a Conductimetric Sensor," Biomaterials for Drug and Cell Delivery, Materials Reserach Society Symposium Proceedings, vol. 331, pp. 193–198 (1994).
Mezei, Michael, "Liposomes as a Skin Drug Delivery System," Topics in Pharmaceutical Sciences pp. 345–357 (1985).
Mitragotri, S. et al., "Synergistic Effect of Low–frequency Ultrasound and Sodium Lauryl Sulfate on Transdermal Transport," 89 J. Pharmaceutical Sciences 892–900 (Jul. 2000).
Miyazaki, et al., "Controlled Drug Release by Ultrasound Irradiation," Chemical & Pharmaceutical Bulletin, 33(1), pp. 428–431 (1985).
Alain Boucaud, et al., "Clinical histologic, and electron microscopy study of skin exposed to low–frequency ultrasound," 264 The Anatomical Record 114–119 (2001).
Otsuka, et al., "Use of Ultrasonic Waves in Pharmacy–I&II. Degradation of Polymers", Chemical Abstracts, vol. 69, No. 20, pp. 7513, Abstract No. 80161r &No. 80162 (Nov. 11, 1968).
"Pharmaceutical Sciences," Chapter 19–Disperse Systems pp. 267–272 Chapter 87–Medicated Applications pp. 1600–1606, 1614 Chapter 91–Sustained–Release Drug Delivery Systems pp. 1690–1693, Mack Publishing Co, Easton PA (1990).
Schreier & Bouwstra, "Liposomes and noisomes as topical drug carriers: dermal and transdermal drug delivery," 30 Journal of Controlled Release 1–15 (1994).
Ahmet Tezel et al., "Synergistic effect of low–frequency ultrasound and surfactants on skin permeability," 91 J. Pharmaceutical Sciences 91–100 (Dec. 14, 2001).
Tang, H. et al., "Theoretical description of transdermal of hydrophilic permeants: application to low–frequency sonophoresis,"90 J. Pharmaceutical Sciences 545–568 (Mar. 28, 2001).

* cited by examiner

SYSTEM, METHOD, AND DEVICE FOR NON-INVASIVE BODY FLUID SAMPLING AND ANALYSIS

CROSS-REFERENCE TO RELATED APPLICATIONS

The present invention claims the benefit of U.S. Provisional Patent Application No. 60/189,971, filed Mar. 17, 2000, the disclosure of which is hereby incorporated by reference in its entireties.

In addition, the invention is related to U.S. patent application Ser. No. 08/885,931, entitled "Ultrasound Enhancement of Transdermal Transport"; U.S. patent application Ser. No. 09/260,265, entitled "Chemical and Physical Enhancers and Ultrasound for Transdermal Drug Delivery"; and PCT International Patent Appl'n Ser. No. PCT/US99/30067, entitled "Method and Apparatus for Enhancement of Transdermal Transport", the disclosures of which are hereby incorporated, by reference, in their entireties.

BACKGROUND OF THE INVENTION

1. Field of the Invention

The present invention relates to non-invasive sampling of body fluids, and, more particularly, to a system, method, and device for non-invasive body fluid sampling and analysis.

2. Description of the Related Art

Diabetics frequently prick their fingers and forearms to obtain blood in order to monitor their blood glucose concentration. This practice of using blood to perform frequent monitoring can be painful and inconvenient. New, less painful methods of sampling body fluids have been contemplated and disclosed. For example, these painless methods include the use of tiny needles, the use of iontophoresis, and the use of ultrasound to sample body fluid, such as blood and interstitial fluid.

It has been shown that the application of ultrasound can enhance skin permeability. Examples of such are disclosed in U.S. Pat. No. 4,767,402, U.S. Pat. No. 5,947,921, and U.S. Pat. No. 6,002,961, the disclosures of which are incorporated, by reference, in their entireties. Ultrasound may be applied to the stratum corneum via a coupling medium in order to disrupt the lipid bilayers through the action of cavitation and its bioacoustic effects. The disruption of stratum corneum, a barrier to transport, allows the enhanced diffusion of analyte, such as glucose or drugs, through, into, and out of the skin.

Transport of analytes and body fluids can be enhanced further by the action of a motive force. These motive forces include, inter alia, sonophoretic, iontophoretic, electromotive, pressure force, vacuum, electromagnetic motive, thermal force, magnetic force, chemomotive, capillary action, and osmotic. The use of active forces provide a means for obtaining fluid for subsequent analysis.

The application of a motive force before, during, and after making the skin permeable has been disclosed in U.S. Pat. No. 5,279,543, U.S. Pat. No. 5,722,397, U.S. Pat. No. 5,947,921, U.S. Pat. No. 6,002,961, and U.S. Pat. No. 6,009,343, the disclosures of which are incorporated by reference in their entireties. The purpose of using a motive force is to actively extract body fluid and its content out of the skin for the purpose of analysis. As mentioned, active forces, such as vacuum, sonophoresis, and electrosmotic forces, can create convective flow through the stratum corneum. Although these forces can be used for extraction of body fluids, there are certain limitations that may apply when the forces are applied to human skin. For example, a major limitation is the flow and volume of body fluid that can be transported across the stratum corneum. In general, high-pressure force is necessary in order to transport fluid across an enhanced permeable area of stratum corneum. The application of vacuum on skin for an extended period may cause physical separation of the epidermis from the dermis, resulting in bruises and blisters.

Another example of a limitation is the amount of energy that can be applied to the skin in order to create convective flow. Extraction of usable volume of body fluid has the potential to cause pain and skin damage with prolonged exposure to ultrasound. In a similar manner, electro-osmotic extraction of body fluid through stratum corneum has the potential to cause skin damage due the need to use high current density. It is evident that there are limitations to the use of the mentioned extraction methods when applied to human skin.

SUMMARY OF THE INVENTION

Therefore, a need has arisen for a system, method, and device for non-invasive body fluid sampling and analysis that overcomes these and other drawbacks of the related art.

Therefore, a need has arisen for a method of enhancing the permeability of a biological membrane, such as skin, buccal, and nails, for an extended period of time, and a method for extracting body fluid to perform blood, interstitial fluid, lymph, or other body fluid analyte monitoring in a discrete or continuous manner that is non-invasive and practical.

A method for non-invasive body fluid sampling and analysis is disclosed. According to one, embodiment of the present invention, the method includes the steps of (1) identifying an area of biological membrane having a permeability level; (2) increasing the permeability level of the area of biological membrane; (3) contacting the area of biological membrane with a receiver; (4) extracting body fluid through and out of the area of biological membrane; (5) providing an external force to enhance the body fluid extraction; (6) collecting the body fluid in the receiver; (7) analyzing the collected body fluid for the presence of at least one analyte; and (8) providing the results of the step of analyzing the body fluid.

The area of biological membrane may be made permeable using ultrasound with controlled dosimetry. Extraction of body fluid may be performed on the area exposed to ultrasound using osmotic transport. The body fluid may be collected using a receiver. The receiver may be attached to the biological membrane in a form of a patch, a wearable reservoir, a membrane, an absorbent strip, a hydrogel, or an equivalent. The receiver may be analyzed for the presence of various analytes indicative of blood analytes. The analysis may comprise the use of electrochemical, biochemical, optical, fluorescence, absorbance, reflectance, Raman, magnetic, mass spectrometry, infra-red (IR) spectroscopy measurement methods and combinations thereof. The receiver may also be attached to a secondary receiver where the concentration of analyte in the secondary receiver is continuously maintained substantially lower than that in the body fluid so the chemical concentration driving force between body fluid and secondary receiver is maximized. This may be achieved by chemical reaction or volume for dilution or similar means. In one embodiment, the receiver and the secondary receiver may operate on different principles (e.g., osmosis, dilution, etc.). In another embodiment, the receivers may operate on the same principle.

A system for non-invasive body fluid sampling and analysis is disclosed. According to one embodiment of the present invention, the system includes a controller that controls the generation of ultrasound; an ultrasonic applicator that applies the ultrasound to an area of biological membrane; a receiver that contacts the area of biological membrane and receives body fluid through and out of the area of biological membrane; and a meter that interacts with the receiver and detects the presence of at least one analyte in the body fluid in the receiver. The receiver may include a membrane and a medium, such as a hydrogel, a fluid, or a liquid, that is contained within the membrane.

A method for noninvasive body fluid sampling and analysis is disclosed. According to one embodiment of the present invention, the method includes the steps of (1) enhancing a permeability level of an area of biological membrane; (2) attaching a receiver to the area of biological membrane; (3) extracting an analyte through and out of the area of biological membrane; (4) collecting the body fluid in the receiver; and (5) determining a concentration of at least one analyte in the body fluid.

A device for noninvasive body fluid sampling and analysis is disclosed. According to one embodiment of the present invention, the device includes a receiver that is attached to an area of biological membrane with an enhanced permeability and receives body fluid through and out of the area of biological membrane, and a wearable meter that detects the presence of at least one analyte in the received body fluid and indicates a concentration of that analyte. The receiver may include a membrane and a medium, such as a hydrogel, a fluid, or a liquid, that is contained in the membrane. The meter may include a processor and a device that detects the presence of the analyte. The detecting device may include an electrochemical detector; a biochemical detector; a fluorescence detector; an absorbance detector; a reflectance detector; a Raman detector; a magnetic detector; a mass spectrometry detector; an IR spectroscopy detector; and combinations thereof.

According to one embodiment of the present invention, osmotic forces may be used to sample body fluid from and through a biological membrane in an on-demand manner. The osmotic agent in solution, gel, hydrogel, or other form may be applied to the ultrasound-treated biological membrane using a receiver, such as a thin liquid reservoir, whenever the concentration of an analyte needs to be determined for diagnosis and monitoring. The receiver may be attached to the biological membrane using an adhesive. The receiver may be attached to the biological membrane for a brief duration. The solution in the receiver may be subsequently removed and analyzed for the presence of analytes. In one embodiment, the receiver may be constructed in the form of a patch. The receiver may contain a hydrogel and osmotic agent. The receiver may combine the osmotic agent and the chemical reagents to detect the presence of the analyte. The reagents may allow the use of electrochemical, biochemical, optical, fluorescence, absorbance, reflectance, Raman, magnetic, mass spectrometry, infrared (IR) spectroscopy measurement methods and combinations thereof to be performed on the receiver.

In another embodiment, osmotic forces may be used to sample body fluid from or through a biological membrane in a periodic or a continuous manner. The osmotic agent in solution form may be applied to the ultrasound-treated biological membrane using a thin receiver, such as a thin liquid reservoir, whenever the concentration of analyte needs to be determined for diagnosis and monitoring. The receiver may be attached to biological membrane using an adhesive. In one embodiment, the receiver may be constructed in the form of a patch. The receiver may contain a hydrogel that contains the osmotic agent. The receiver may contain means for manipulating the intensity and duration of the osmotic force. The intensity of the osmotic force may be manipulated using electric field forces, magnetic field forces, electromagnetic field forces, biochemical reactions, chemicals, molarity adjustment, adjusting solvents, adjusting pH, ultrasonic field forces, electro-omostic field forces, iontophoretic field forces, electroporatic field forces and combinations thereof. The duration of the osmotic force may be manipulated using electric field forces, magnetic field forces, electromagnetic field forces, biochemical reactions, chemicals, molarity adjustment, adjusting solvents, adjusting pH, ultrasonic field forces, electroomostic field forces, iontophoretic field forces, electroporatic field forces and combinations thereof. The receiver may combine the osmotic agent and the biochemical reagents to detect the presence of the analyte. The reagents may allow the use of electrochemical, biochemical, optical, fluorescence, absorbance, reflectance, Raman, magnetic, mass spectrometry, IR spectroscopy measurement methods and combinations thereof to be performed on the receiver. The receiver may also be removed periodically for detection.

In one embodiment, the intensity, duration, and frequency of exposure of biological membrane to osmotic forces may be manipulated by using an electric current to cause a change in the concentration of the osmotic agent that is in contact with the ultrasound-exposed biological membrane. The osmotic agent may be a multi-charged agent that can dissociate into several charged species. These charged species may be transported using electric field forces. A membrane may be used to isolate the charged species. The charged species freely diffuse and combine upon removal of the electric field force.

In one embodiment, the intensity, duration, and frequency of exposure of biological membrane to osmotic forces may be manipulated by using active forces to cause a change in the concentration of the osmotic agent that is in contact with the ultrasound-exposed biological membrane. The osmotic agent may be a neutral charge agent. The agent may be transported using a variety of field forces. The field force depends on the constitutive and colligative properties of the chosen agent. The field force generates a force necessary to move the osmotic agent toward and away from the biological membrane surface. The movement of the osmotic agent modulates the periodic and continuous extraction of body fluid through the stratum corneum.

In one embodiment, the intensity, duration, and frequency of exposure of biological membrane to osmotic forces may be manipulated by changing the concentration of the osmotic agent that is in contact with the ultrasound-exposed biological membrane. Manipulating the volume of the solvent and the volume of the hydrogel containing the osmotic agent may cause a change in the concentration of the osmotic agent. The volume of the hydrogel can be changed by constructing a hydrogel wherein its volume is sensitive to the concentrations of molecules that can diffuse into the gel. One example is a hydrogel constructed to be sensitive to the molecule glucose. The hydrogel volume can also be changed by manipulating its temperature and by changing the pH of the gel.

A receiver that is attached to an area of biological membrane with an enhanced permeability and receives body fluid through and out of the area of biological membrane is disclosed. According to one embodiment of the present invention, the receiver includes a first grid; a medium layer comprising at least one agent; a membrane that induces a concentration gradient barrier for the at least one agent; a counter grid; an oxidase layer; a detection layer; and a voltage source that provides a potential difference between the first grid and the counter grid. The body fluid, which may include blood, interstitial fluid, analyte, and lymph, may flow out of, or through, the biological membrane, to the detector layer via the first grid, the counter grid, and the oxidase layer.

It is a technical advantage of the present invention that a system, method, and device for non-invasive sampling and analysis of body fluids is disclosed. It is another technical advantage of the present invention that a concentration of an analyte may be measured continuously or periodically.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF THE INVENTION

The preferred embodiment of the present invention and its advantages are best understood by referring to FIGS. 1 through 7 of the drawings, like numerals being used for like and corresponding parts of the various drawings.

As used herein, the term "body fluid" may include blood, interstitial fluid, lymph, and/or analyte. In addition, as used herein, the term "biological membrane" may include tissue, mucous membranes and cornified tissues, including skin, buccal, and nails. Further, as used herein, the term "force" may also include force gradients.

Although the present invention may be described in conjunction with human applications, veterinary applications are within the contemplation and the scope of the present invention.

Figure 1:
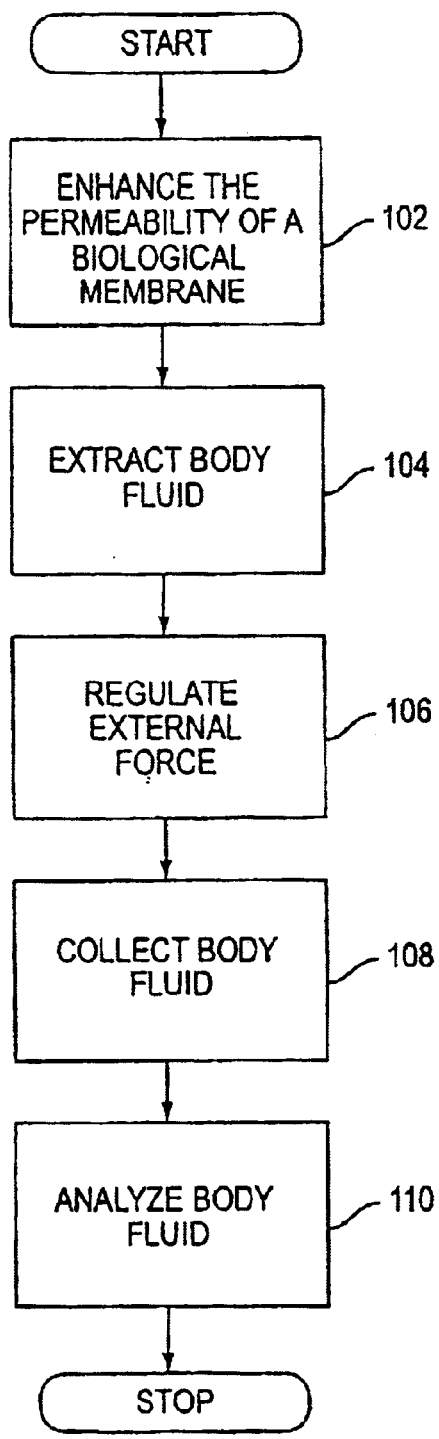
FIG. 1 is a flowchart depicting a method for non-invasive body fluid sampling according to one embodiment of the present invention.

Referring to FIG. 1, a flowchart depicting a method for non-invasive body fluid sampling and analysis according to one embodiment of the present invention is provided. In step 102, the permeability of an area of biological membrane is enhanced. In one embodiment, the area of biological membrane may be located on the volar forearm of a mammalian subject. In another embodiment, the area of biological membrane may be located on a thigh of a mammalian subject. In yet another embodiment, the area of biological membrane may be located on the abdomen. In still another embodiment, the area of biological membrane may be located on the back. Other body locations may also be used.

In general, several techniques may be used to enhance the permeability of the biological membrane, such as creating physical micropores, physically disrupting the lipid bilayers, chemically modifying the lipid bilayers, physically disrupting the stratum corneum, and chemically modifying the stratum corneum. The creation of micropores, or the disruption thereof, may be achieved by physical penetration using a needle, a microneedle, a silicon microneedle, a laser, a laser in combination with an absorbing dye, a heat source, an ultrasonic needle, an ultrasonic transducer, cryogenic ablation, RF ablation, photo-acoustic ablation, and combinations thereof.

In a preferred embodiment, ultrasound may be applied to the area of biological membrane to enhance its permeability. Ultrasound is generally defined as sound at a frequency of greater than about 20 kHz. Therapeutic ultrasound is typically between 20 kHz and 5 MHz. Near ultrasound is typically about 10 kHz to about 20 kHz. It should be understood that in addition to ultrasound, near ultrasound may be used in embodiments of the present invention.

In general, ultrasound, or near ultrasound, is preferably applied to the area of biological membrane at a frequency sufficient to cause cavitation and increase the permeability of the biological membrane. In one embodiment, ultrasound may be applied at a frequency of from about 10 kHz to about 500 kHz. In another embodiment, ultrasound may be applied at a frequency of from about 20 kHz to about 150 kHz. In yet another embodiment, the ultrasound may be applied at 50 kHz. Other frequencies of ultrasound may be applied to enhance the permeability level of the biological membrane.

In one embodiment, the ultrasound may have an intensity in the range of about 0 to about 100 watt/cm$^2$, and preferably in the range of 0 to about 20 watt/cm$^2$. Other appropriate intensities may be used as desired.

Techniques for increasing the permeability of a biological membrane are disclosed in U.S. Pat. No. 6,190,315 to Kost et al., the disclosure of which is hereby incorporated by reference in its entirety.

In step 104, body fluid is extracted through or out of the area of biological membrane. In one embodiment, an external force, such as an osmotic force, may assist in the extraction. In one embodiment, the osmotic force may be controlled before, during, and after the permeability of the biological membrane is enhanced.

In one embodiment, the osmotic force may be generated by the application of an osmotic agent to the area of biological membrane. The osmotic agent may be in the form of an element, a molecule, a macromolecule, a chemical compound, or combinations thereof. The osmotic agent may also be combined with a liquid solution, a hydrogel, a gel, or an agent having a similar function.

In step 106, the magnitude, intensity, and duration of the external force may be regulated by at least one additional first energy and/or force. In one embodiment, the first additional energy and/or force may be applied to control and regulate the movement and function of the osmotic agent for extraction of body fluid through and out of the biological membrane. The first additional energy and/or force may be provided in the form of heat, a temperature force, a pressure force, an electromotive force, a mechanical agitation, ultrasound, iontophoresis, an electromagnetic force, a magnetic force, a photothermal force, a photoacoustic force, and combinations thereof. The effect of an electric field and ultrasound on transdermal drug delivery is disclosed in U.S. Pat. No. 6,041,253, the disclosure of which is incorporated, by reference, in its entirety.

In one embodiment, if the first additional energy and/or force is provided by ultrasound, the frequency of the ultrasound may be provided at a different frequency than the frequency used to enhance the permeability of the biological membrane. In one embodiment, the frequency of the first additional energy/force ultrasound may be higher than the frequency of the permeability enhancing ultrasound.

In step 108, the body fluid may be collected in a receiver. In one embodiment, the receiver may be contacted with the biological membrane in a form of a patch, a wearable reservoir, a membrane, an absorbent strip, a hydrogel, or a structure that performs an equivalent function. Other types and configurations of receivers may be used.

In one embodiment, the receiver may be provided with a secondary receiver having an analyte concentration that is continuously maintained to be substantially lower than the analyte concentration in the body fluid, so the chemical concentration driving force between body fluid and secondary receiver is maximized. This may be achieved by chemical reaction or volume for dilution or similar means.

In one embodiment, a second external energy/force may be applied between the first receiver and the secondary receiver. In one embodiment, the second external energy/force may be different (e.g., a different type of external force) from the first external energy/force. In another embodiment, the second external energy/force may be the same (e.g., the same type of external force) as the first external energy/force. The first and second external energy/force may vary in type, duration, and intensity, and may be controlled through different additional energy and/or forces.

In step 110, the collected body fluid may be analyzed. In one embodiment, the analysis may include the use of appropriate methods, such as electrochemical, biochemical, optical, fluorescence, absorbance, reflectance, Raman, magnetic, mass spectrometry, infra-red (IR) spectroscopy measurement, and combinations thereof.

In one embodiment, multiple analytes may be analyzed simultaneously, in parallel, or in series. The results from these multiple analyses may be used in combination with algorithms, for example, to increase the accuracy, or precision, or both, of the analysis and measurements.

In one embodiment, the receiver may be removed from contact with the biological membrane in order to analyze the collected body fluid. In another embodiment, the receiver may remain in contact with the biological membrane as the collected body fluid is analyzed.

Figure 2:
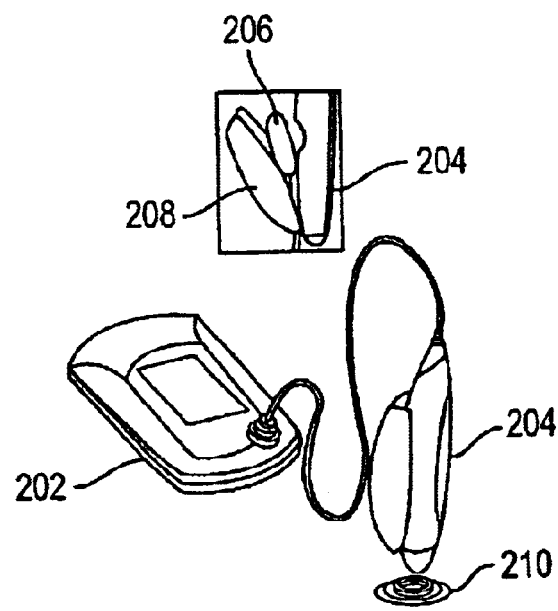
FIG. 2 depicts a device for controlled application of ultrasound to a biological membrane to enhance the permeability of the biological membrane according to one embodiment of the present invention.

Referring to FIG. 2, a device for the controlled application of ultrasound to biological membrane to enhance the permeability of a biological membrane according to one embodiment of the present invention is shown. Device 200 includes controller 202, which interfaces with ultrasound applicator 204 by any suitable means, such as a cable. Controller 202 controls the application of ultrasound to the area of biological membrane. In one embodiment, ultrasound or near ultrasound having an intensity in the range of about 0 to about 20 watt/cm$^2$ may be generated by controller 202 and ultrasound applicator 204. In one embodiment, the ultrasound may have a frequency of about 20 kHz to about 150 kHz. In another embodiment, the ultrasound may have a frequency of 50 kHz. Other ultrasound frequencies may also be used.

In addition, controller 202 may include a display, such as a LCD or a LED display, in order to convey information to the user as required. Controller 202 may also include a user interface as is known in the art.

Ultrasound applicator 204 may be provided with cartridge 206, which contains ultrasound coupling solution 208. Cartridge 206 may be made of any material, such as plastic, that may encapsulate ultrasound coupling solution 208. Suitable ultrasound coupling solutions 208 include, but is not limited to, water, saline, alcohols including ethanol and isopropanol (in a concentration range of 10 to 100% in aqueous solution), surfactants such as Triton X-100, SLS, or SDS (preferably in a concentration range of between 0.001 and 10% in aqueous solution), DMSO (preferably in a concentration range of between 10 and 100% in aqueous solution), fatty acids such as linoleic acid (preferably in a concentration range of between 0.1 and 2% in ethanol-water (50:50) mixture), azone (preferably in a concentration range of between 0.1 and 10% in ethanol-water (50:50) mixture), polyethylene glycol in a concentration range of preferably between 0.1 and 50% in aqueous solution, histamine in a concentration range of preferably between 0.1 and 100 mg/ml in aqueous solution, EDTA in a concentration range of preferably between one and 100 mM, sodium hydroxide in a concentration range of preferably between one and 100 mM, sodium octyl sulfate, N-lauroylsarcosine, octyltrimethyl ammoniumbromide, dodecyltrimethyl ammoniumbromide, tetradecyltrimethyl ammoniumbromide, hexadecyltrimethyl ammoniumbromide, dodecylpyridinium chloride hydrate, SPAN 20, BRIJ 30, glycolic acid ethoxylate 4-ter-butyl phenyl ether, IGEPAL CO-210, and combinations thereof.

In one embodiment, the coupling medium may also include a chemical enhancer. Transport enhancement may be obtained by adding capillary permeability enhancers, for example, histamine, to the coupling medium. The concentration of histamine in the coupling medium may be in the range of between 0.1 and 100 mg/ml. These agents may be delivered across the biological membrane during application of ultrasound and may cause local edema that increases local fluid pressure and may enhance transport of analytes across the biological membrane. In addition, the occurrence of free fluid due to edema may induce cavitation locally so as to enhance transport of analytes across the biological membrane.

In one embodiment, cartridge 206 may be pierced when inserted into ultrasound applicator 204, and ultrasound coupling solution 208 may be transferred to a chamber (not shown).

A target identifying device, such as target ring 210, may be attached to the area of biological membrane that will have its permeability increased. Target ring 210 may be attached to the area of biological membrane by a transdermal adhesive (not shown). In one embodiment, target ring 210 may have the transdermal adhesive pre-applied, and may be disposed after each use. In another embodiment, target ring 210 may be reusable.

Target ring 210 may be made of any suitable material, including plastic, ceramic, rubber, foam, etc. In general, target ring 210 identifies the area of biological membrane for permeability enhancement and body fluid extraction. In one embodiment, target ring 210 may be used to hold receiver 214 in contact with the biological membrane after the permeability of the biological membrane has been increased.

In one embodiment, target ring 210 may be used to monitor the permeability level of the biological membrane, as disclosed in PCT International Patent Appl'n Ser. No. PCT/US99/30067, entitled "Method and Apparatus for Enhancement of Transdermal Transport," the disclosure of which is incorporated by reference in its entirety. In such an embodiment, target ring 210 may interface with ultrasound applicator 204.

Ultrasound applicator 204 may be applied to target ring 210 and activated to expose ultrasound coupling solution 208 to the biological membrane. Controller 202 controls ultrasound applicator 204 to transmit ultrasound through ultrasound coupling solution 208. During ultrasound exposure, controller 202 may monitor changes in biological membrane permeability, and may display this information to the user.

Controller 202 may cease, or discontinue, the application of ultrasound once a predetermined level of biological membrane permeability is reached. This level of permeability may be preprogrammed, or it may be determined in real-time as the ultrasound is applied. The predetermined level of permeability may be programmed for each individual due to biological membrane differences among individuals.

After the predetermined level of permeability is reached, ultrasound coupling solution 208 may be vacuated from chamber (not shown) into cartridge 206, which may then be discarded. In another embodiment, ultrasound coupling solution 208 may be vacuated into a holding area (not shown) in ultrasound applicator 204, and later discharged. Ultrasound applicator 204 may then be removed from target ring 210.

Figure 3:
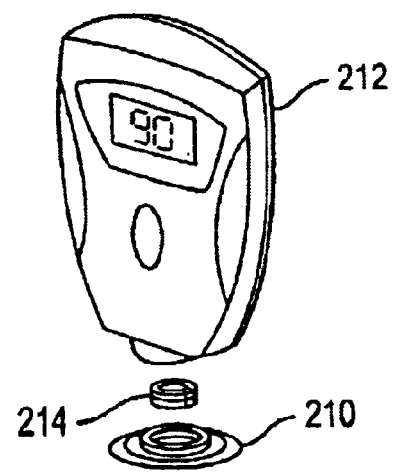
FIG. 3 depicts the components to perform discrete extraction and measurement of body fluid to infer analyte concentrations according to one embodiment of the present invention.

Referring to FIG. 3, an device for the analysis of body fluid according to one embodiment of the present invention is provided. Receiver 214 may be placed into target ring 210 to perform a discrete, or on-demand, extraction of body fluid through and/or out of the biological membrane. Receiver 214 may contain a medium, such as a hydrogel layer, that incorporates an osmotic agent. In one embodiment, the hydrogel may be formulated to contain phosphate buffered saline (PBS), with the saline being sodium chloride having a concentration range of about 0.01 M to about 10 M. The hydrogel may be buffered at pH 7. Other osmotic agents may also be used in place of, or in addition to, sodium chloride. Preferably, these osmotic agents are non-irritating, non-staining, and non-immunogenic. Examples of such osmotic agents include, inter alia, lactate and magnesium sulfate.

In another embodiment, receiver 214 may include a fluid or liquid medium, such as water or a buffer, that is contained within a semi-permeable membrane. Receiver 214 may also include a spongy material, such as foam.

Receiver 214 may be applied to the biological membrane to contact the ultrasound exposed biological membrane. In one embodiment, receiver 214 may be applied to the biological membrane for a time period sufficient to collect an amount of body fluid sufficient for detection. In another embodiment, receiver 214 may be applied to the biological membrane for a sufficient time period to collect a predetermined amount of body fluid. In yet another embodiment, receiver 214 may be applied to the biological membrane for a predetermined time. In one embodiment, the contact between receiver 214 and the biological membrane may last for 15 minutes or less. In another embodiment, the contact between receiver 214 and the biological membrane may last for 5 minutes or less. In still another embodiment, the contact between receiver 214 and the biological membrane may last for 2 minutes or less. The actual duration of contact may depend on the sensitivity of the detection method used for analysis.

In one embodiment, the medium of receiver 214 may contain at least one reagent (not shown) in order to detect the presence of certain analytes in the body fluid that has been extracted from or through the biological membrane. In one embodiment, the hydrogel layer of receiver 214 may contain the reagents, and the reagents may be attached to the hydrogel by ionic and/or covalent means, or may be immobilized by gel entrapment. The reagents may also be arranged as an adjacent layer to the hydrogel wherein the analyte from the body fluid that has been extracted into the hydrogel can diffuse into and react to generate by-products. The by-products may then be detected using electrochemical, biochemical, optical, fluorescence, absorbance, reflectance, Raman, magnetic, mass spectrometry, IR spectroscopy measurement methods and combinations thereof.

The detection methods may be performed by meter 212. Meter 212 may include a processor (not shown) and a display, such as an LCD display. Other suitable displays may be provided.

In one embodiment, meter 212 may provide an interface that allows information be downloaded to an external device, such as a computer. Such an interface may allow the connection of interface cables, or it may be a wireless interface.

Meter 212 may be configured to determine body fluid glucose concentration by incorporating glucose oxidase in the medium of receiver 214. In one embodiment, glucose from extracted body fluid may react with glucose oxidase to generate hydrogen peroxide. Hydrogen peroxide may be detected by the oxidation of hydrogen peroxide at the surface of electrodes incorporated into receiver 214. The oxidation of hydrogen peroxide transfers electrons onto the electrode surface which generates a current flow that can be quantified using a potentiostat, which may be incorporated into meter 212. A glucose concentration proportional to the concentration of hydrogen peroxide may be calculated, and the result may be reported to the user via a display. Various configurations of electrodes and reagents, known to those of ordinary skill in the art, may be incorporated to perform detection and analysis of glucose and other analytes.

Meter 212 may also be configured to simultaneously measure the concentration of an analyte, such as glucose, where the body fluid concentration is expected to fluctuate, and an analyte, like creatinine or calcium, where the body fluid concentration is expected to remain relatively stable over minutes, hours, or days. An analyte concentration, which may be determined by an algorithm that takes into account the relative concentrations of the fluctuating and the more stable analyte, may be reported to the user via a display.

In another embodiment, meter 212 may analyze multiple analytes simultaneously, in parallel, or in series. The results from these multiple analyses may be used in combination with algorithms, for example, to increase the accuracy, or precision, or both, of the analysis and measurements.

Receiver 214 may be discarded after the extraction and measurement steps. In another embodiment, receiver 214 may be reused. In one embodiment, receiver 214 may be cleaned, sanitized, etc. before it may be reused. Various configurations of electrodes and reagents, known to those of ordinary skill in the art, may be incorporated to perform detection and analysis of glucose and other analytes.

Figure 4:
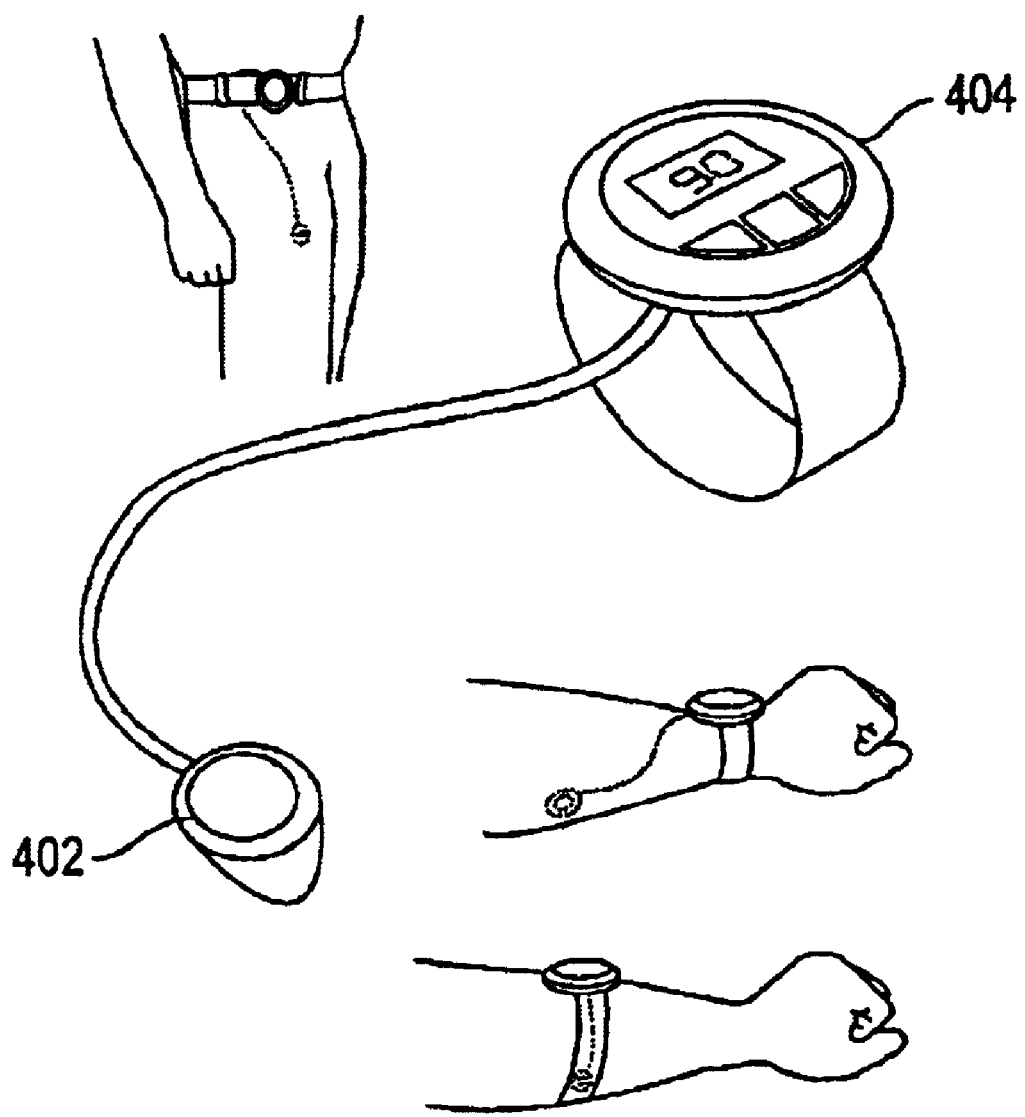
FIG. 4 depicts the components to perform continuous extraction and measurement of body fluid to infer analyte concentrations according to one embodiment of the present invention.

Referring to FIG. 4, an device for the continuous extraction and analysis of body fluid to infer analyte concentrations according to another embodiment of the present invention is provided. As shown in the figure, a biological membrane site on the forearm, the abdomen, or thigh may be exposed to ultrasound; other biological membrane sites, such as those on the back, may also be used. Receiver 402, which may be similar to receiver 214, may contact the ultrasound exposed biological membrane site to perform continuous extraction of body fluid. In one embodiment, receiver 402 may contain a medium, such as a hydrogel layer, that may incorporate an osmotic agent, such as sodium chloride. The hydrogel is formulated to contain phosphate buffered saline (PBS), with the saline being sodium chloride in the concentration range of 0.01 M to 10 M. The hydrogel may be buffered at pH 7.

Other osmotic agents may also be used in place of, or in addition to, sodium chloride. These osmotic agents are preferably non-irritating, non-staining, and non-immunogenic. Examples of these other osmotic agents may include, inter alia, lactate and magnesium sulfate. Receiver 402 may be applied to contact the ultrasound exposed biological membrane. In one embodiment, the duration of this contact may be 12–24 hours, or more. In another embodiment, other durations of contact, including substantially shorter durations, and substantially longer durations, may be used as desired.

In another embodiment, receiver 402 may include a fluid or liquid medium, such as water or a buffer, that is contained within a semi-permeable membrane. Receiver 402 may also include a spongy material, such as foam.

In one embodiment, the medium of receiver 402 may contain at least one reagent (not shown) that detects the presence of analytes in the body fluid that has been extracted thorough and out of the biological membrane. In one embodiment, the hydrogel layer of receiver 402 may contain reagents that may be attached by ionic and covalent means to the hydrogel, or may be immobilized by gel entrapment. The reagents may also be arranged as an adjacent layer to the hydrogel wherein the analyte from the body fluid that has been extracted into the hydrogel may diffuse into and react to generate by-products. The by-products may be detected using electrochemical, biochemical, optical, fluorescence, absorbance, reflectance, Raman, magnetic, mass spectrometry, IR spectroscopy measurement methods and combinations thereof.

The detection methods and results may be performed and presented to the user by meter 404, which may be similar in function to meter 212, discussed above. In one embodiment, meter 404 may be wearable. For example, as depicted in the figure, meter 404 may be worn a manner similar to the way a wristwatch is worn. Meter 404 may also be worn on a belt, in a pocket, etc.

Meter 404 may incorporate power and electronics to control the periodic extraction of body fluid, to detect analyte, and to present the analyte concentration in a continuous manner. Meter 404 may contain electronics and software for the acquisition of sensor signals, and may perform signal processing, and may store analysis and trending information.

In one embodiment, meter 404 may provide an interface that allows information be downloaded to an external device, such as a computer. Such an interface may allow the connection of interface cables, or it may be a wireless interface.

Meter 404 may be configured to determine body fluid glucose concentration by incorporating glucose oxidase in the medium. In one embodiment, glucose from extracted body fluid may react with glucose oxidase to generate hydrogen peroxide. Hydrogen peroxide may be detected by the oxidation of hydrogen peroxide at the surface of electrodes incorporated into receiver 402. The oxidation of hydrogen peroxide transfers electrons onto the electrode surface which generates a current flow that can be quantified using a potentiostat, which may be incorporated into meter 404. A glucose concentration proportional to the concentration of hydrogen peroxide may be calculated and the result may be reported to the user via a display. Various configurations of electrodes and reagents, known to those of ordinary skill in the art, may be incorporated to perform detection and analysis of glucose and other analytes.

In one embodiment, meter 404 may also be configured to simultaneously measure concentration of an analyte, such as glucose, where the body fluid concentration is expected to fluctuate, and an analyte, like creatinine or calcium, where the body fluid concentration is expected to remain relatively stable over minutes, hours, or days. An analyte concentration, which may be determined by an algorithm that takes into account the relative concentrations of the fluctuating and the more stable analyte, may be reported to the user via a display.

In another embodiment, meter 404 may analyze multiple analytes simultaneously, in parallel, or in series. The results from these multiple analyses may be used in combination with algorithms, for example, to increase the accuracy, or precision, or both, of the analysis and measurements.

In another embodiment, receiver 402 may be removed from contact with the biological membrane for analysis by meter 404. Receiver 402 may be put in contact with the biological membrane after such analysis.

Meter 404 may provide analyte readings to the user in a periodic or a continuous manner. For example, in one embodiment, in continuous monitoring of the analyte glucose, glucose concentration may be displayed to the user every 30 minutes, more preferably every 15 minutes, most preferable every 5 minutes, or even more frequently. In another embodiment, the glucose concentration may be displayed continuously. The period may depend on the sensitivity and method of analyte detection. In continuous glucose monitoring, in one embodiment, glucose detection may be performed by an electrochemical method using electrodes and reagents incorporated into receiver 402 and detection and analysis performed by meter 404. During the measurement period, osmotic extraction of body fluid may be performed continuously by the hydrogel layer of receiver 402. Body fluid may accumulate in the hydrogel of receiver 402. Glucose in body fluid diffuses to react with glucose oxidase and is converted into hydrogen peroxide. The hydrogen peroxide is consumed by poising the working electrode with respect to a reference electrode. During the resting period, hydrogen peroxide accumulates and is consumed or destroyed before the measuring period. The magnitude of the working potential can be applied to rapidly consume the build up of hydrogen peroxide.

Figure 5:
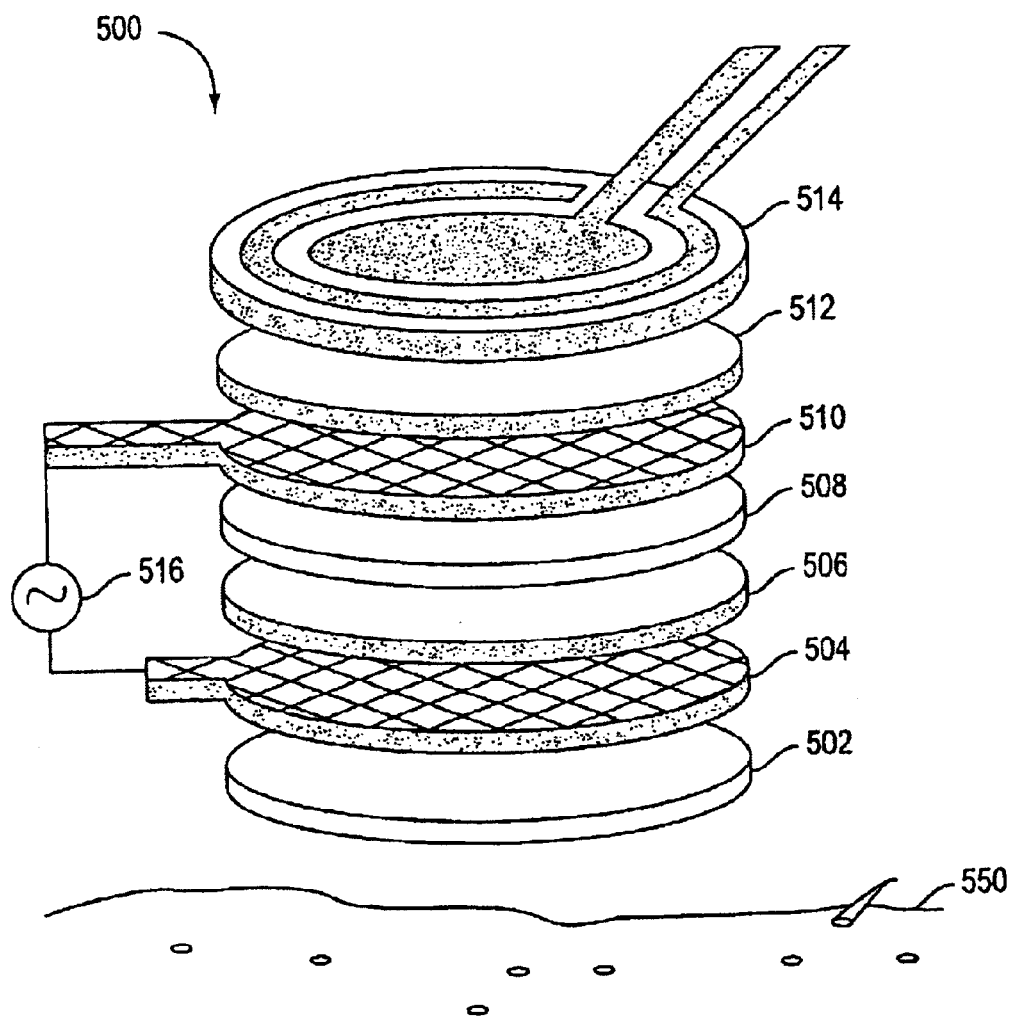
FIG. 5 depicts an approach to periodic monitoring of an analyte by performing periodic osmotic extractions of body fluid according to one embodiment of the present invention.

Referring to FIG. 5, an approach to periodic monitoring of an analyte by performing periodic osmotic extractions of body fluid according to another embodiment of the present invention is shown. The osmotic extraction intensity and frequency may be manipulated by using an osmotic agent that dissociates into multiple charged species, and an electrical potential may be used to move the concentration of charges toward and away from biological membrane surface 550. Receiver 500 may include grid, mesh, or screen 504; medium 506, which may be a hydrogel layer; membrane 508; counter grid, mesh, or screen 510; oxidase layer 512; and detection layer 514. Grid 504 and counter grid 510 may be connected to voltage source 516. Membrane 508 may be a semi-permeable membrane that is used to induce a concentration gradient barrier for the osmotic agent contained in medium 506. The preferable osmotic agent may contain negative and positive species or counter ions. Manipulating the concentration of charged species at the boundary adjacent to the stratum corneum of the ultrasound-exposed biological membrane may provide periodic extraction of body fluid.

In one embodiment, receiver 500 may make contact with the skin though contact medium 502, which may be a hydrogel, or other suitable medium.

The concentration of the charged species may be manipulated by applying a potential difference between grid 504 and counter grid 510 using voltage source 516. In one embodiment, the potential difference may be of a magnitude that is sufficient to manipulate the osmotic agent. The polarity of the grid may also be changed to transport charges toward and away from biological membrane surface 550. Grid 504 and counter grid 510 may be configured with optimum porosity as to allow body fluid and/or analyte to travel out of stratum corneum, through grid 504, through grid 510, and into oxidase layer 512, and ultimately to detection layer 514. Oxidase layer 512 may be used with an appropriate catalyst, or enzyme, to confer specificity of analyte detection. Detection layer 514 may include working and reference electrodes (not shown) that allow for the detection of the by-products of oxidase layer 512 to quantify the concentration of the desired analyte of detection.

EXAMPLE

In order to better understand the present invention, an example is provided. The example does not limit the present invention in any way, and is intended to illustrate an embodiment of the present invention.

The following is a description of experiments which implemented painless extraction, collection, and analysis of body fluid to determine body fluid glucose concentration in a human using a hyperosmotic extraction fluid and comparing this condition with iso-osmotic extraction fluid, in accordance with one embodiment of the present invention. Although body fluid glucose concentration serves as an example to demonstrate feasibility, other analytes are within the contemplation of the present invention. In addition, multiple analytes may be measured and/or analyzed simultaneously, in parallel, or in series, and results from these multiple measurements may be used in combination with algorithms, for example, to increase the accuracy or precision or both of measurements. As may be recognized by one of ordinary skill in the art, these steps may be automated and implemented with the device described above.

Four sites on the volar forearm of a human volunteer were treated with ultrasound using the device described in FIG. 2. The ultrasound transducer and its housing were placed on the volar forearm of the volunteer with enough pressure to produce a good contact between the skin and the outer transducer housing, and to prevent leaking. The area surrounding the transducer was then filled with a coupling medium of sodium dodecyl sulfate and silica particles in phosphate-buffered saline (PBS). Ultrasound was briefly applied (5-30 s), the transducer apparatus was removed from the biological membrane, and the skin was rinsed with tap water and dried.

Figure 6:
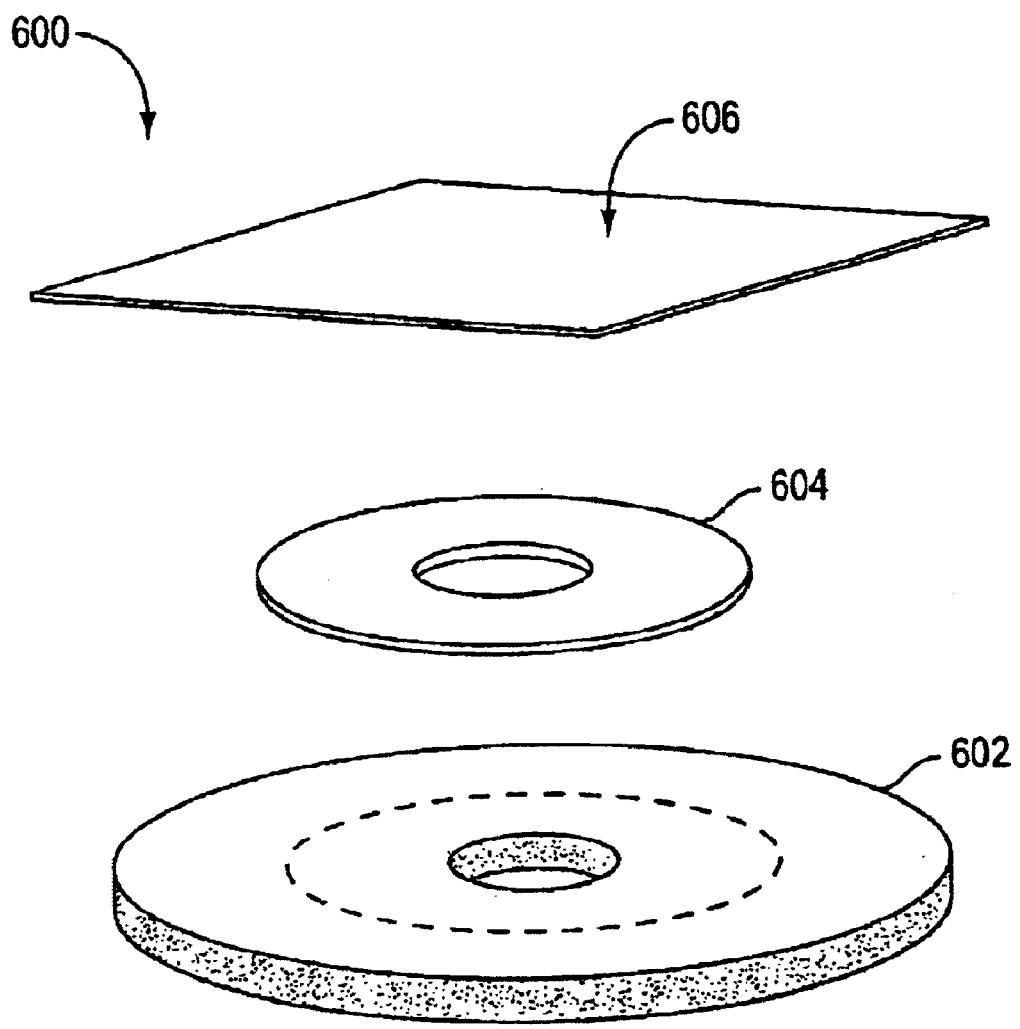
FIG. 6 depicts the components of a wearable extraction chamber according to one embodiment of the present invention.

FIG. 6 describes the components of wearable extraction chamber 600. Four extraction chambers were placed on each sonicated site of the human volunteer. Thin circular foam chamber 602 was constructed using foam MED 5636 Avery Dennison (7/16" ID×1⅛" OD). Foam chambers 602 were attached concentrically to the sonicated biological membrane sites using double-sided adhesive (Adhesive Arcade 8570, 7/16" ID×⅞" OD) attached to one side of element 602. The other side of foam chamber 602 was attached concentrically to double-sided adhesive 604 (Adhesive Arcade 8570, 7/16" ID×⅞" OD). Thin transparent lid 606 was made of 3M Polyester 1012 (1⅛"×1⅛"). Double-sided adhesive 604 permitted thin transparent lid 606 to be attached to foam chamber 602 after placement of liquid into the inner diameter of foam chamber 602 when attached to biological membrane. Thin transparent lid 606 acted as a lid to prevent liquid from leaking out of the extraction chamber, and to allow the extraction chambers to be wearable for an extended period of time.

Each extraction chamber was alternately filled with 100 μl of extraction solution for 15 min and 100 μl hydration solution for 10–40 min. Extraction solution was PBS; on two sites the PBS contained additional NaCl to bring the total concentration of NaCl to 1 M. Hydration solution was PBS for all sites.

Figure 7:
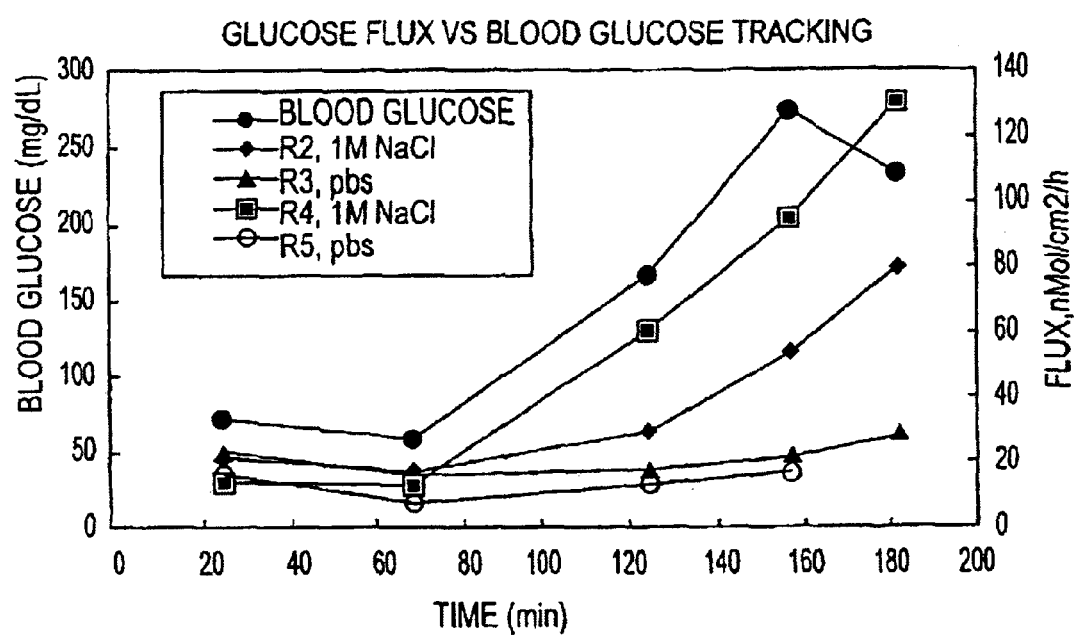
FIG. 7 depicts a graph of glucose flux versus blood glucose concentration according to one embodiment of the present invention.

Solutions were collected and analyzed for glucose concentration using high-pressure liquid chromatography. The results of the HPLC concentration were normalized for the injection amount and the total solution volume, and were reported as glucose flux ($Q_g$), the mass of glucose that crossed the sonicated site per unit time per unit area. Body fluid glucose concentrations ($C_{bg}$) were obtained by testing capillary blood obtained from a lanced finger in a Bayer Glucometer Elite meter. It was hypothesized that $Q_g$ would be linearly proportional to $C_{bg}$. FIG. 7 shows a graph of $Q_g$ versus $C_{bg}$. Unexpectedly, $Q_g$ from the sonicated sites exposed to 1 M NaCl correlated to $C_{bg}$ much more strongly than $Q_g$ from the sonicated sites exposed to 0.15 M NaCl.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. A method for non-invasive body fluid sampling and analysis, comprising:

identifying an area of biological membrane having a permeability level;

increasing the permeability level of the area of biological membrane by applying ultrasound having a frequency range of from about 10 kHz to about 500 kHz to the area of biological membrane;

contacting the area of biological membrane with a receiver;

extracting at least one analyte of the body fluid through and out of the area of biological membrane and into the receiver;

providing an external force to enhance the extraction of the at least one analyte;

continuously analyzing the at least one analyte; and providing the results of the step of continuously analyzing the at least one analyte.

2. The method of claim 1, wherein the step of increasing the permeability level of the area of biological membrane comprises:

applying ultrasound having a frequency range of from about 20 kHz to about 150 kHz to the area of biological membrane.

3. The method of claim 1, wherein the step of increasing the permeability level of the area of biological membrane comprises:

applying ultrasound having a frequency of about 50 kHz to the area of biological membrane.

4. The method of claim 1, wherein the step of increasing the permeability level of the area of biological membrane comprises:

increasing the permeability level of the area of biological membrane to a predetermined level.

5. The method of claim 1, wherein the step of increasing the permeability level of the area of biological membrane comprises:

increasing the permeability level of the biological membrane with a method selected from the group consisting of: creating physical micropores in the area of biological membrane; physically disrupting lipid bilayers in the area of biological membrane; chemically modifying lipid bilayers in the area of biological membrane; physically disrupting the stratum corneum in the area of biological membrane; and chemically modifying the stratum corneum in the area of biological membrane.

6. The method of claim 1, wherein the step of providing an external force to enhance the extraction of the at least one analyte comprises:

generating at least one osmotic force to enhance the extraction of the at least one analyte.

7. The method of claim 6, wherein the step of generating at least one osmotic force to enhance the extraction of the at least one analyte comprises:

generating the at least one osmotic force by applying at least one osmotic agent to the area of biological membrane.

8. The method of claim 1, wherein the step of continuously analyzing the at least one analyte comprises:

providing the receiver with at least one reagent that facilitates the measurement of analyte flux for the at least one analyte.

9. The method of claim 1, wherein the step of continuously analyzing the at least one analyte comprises:

using a method selected from the group consisting of electrochemical, biochemical, optical, fluorescence, absorbance, reflectance, Raman, magnetic, mass spectrometry, IR spectroscopy measurement methods, and combinations thereof to measure analyte flux for the at least one analyte.

10. The method of claim 1, wherein the step of continuously analyzing the at least one analyte comprises:

providing a meter to analyze the at least one analyte using a method selected from the group consisting of electrochemical, optical, fluorescence, absorbance, reflectance, Raman, magnetic mass spectrometry, IR spectroscopy measurement methods, and combinations therof.

11. The method of claim 1, wherein the step of continuously analyzing the at least one analyte at least comprises:

determining an analyte flux for the at least one analyte from the body fluid.

12. The method of claim 1, wherein the step of providing the results of the step of analyzing the at least one analyte comprises:

displaying the results of the step of analyzing the at least one analyte.

13. The method of claim 1, wherein said analyte is glucose.

14. A method for non-invasive body fluid sampling and analysis, comprising:

identifying an area of biological membrane having a permeability level;

increasing the permeability level of the area of biological membrane;

contacting the area of biological membrane with a receiver;

extracting at least one analyte of the body fluid through and out of the area of biological membrane and into the receiver;

providing an external force to enhance the extraction of the at least ne analyte;

analyzing the at least one analyte; and providing the results of the step of analyzing the at least one analyte;

wherein the step of identifying an area of biological membrane having a permeability level comprises: providing a target identifying device to the area of biological membrane.

15. A method for non-invasive body fluid sampling and analysis, comprising:

identifying an area of biological membrane having a permeability level;

increasing the permeability level of the area of biological membrane;

contacting the area of biological membrane with a receiver;

extracting at least one analyte of the body fluid through and out of the area of biological membrane and into the receiver;

providing an external force to enhance the extraction of the at least one analyte;

analyzing the at least one analyte;

providing the results of the step of analyzing the at least one analyte;

providing the receiver with a second receiver, the second receiver having a concentration of the at least one analyte; and maintaining the concentration of the at least one analyte in the second receiver at a level that is lower than a concentration of the extracted at least one analyte.

16. The method of claim 15, further comprising the step of:

providing a second external force to the second receiver.

17. The method of claim 16, wherein the first external force and the second external force differ in at least one of a type, duration, and an intensity.

18. A method for non-invasive body fluid sampling and analysis, comprising:

identifying an area of biological membrane having a permeability level;

increasing the permeabiligy level of the area of biologial membrane;

contacting the area of biological membrane with a receiver;

extracting at least one analyte of the body fluid through and out of area of biological membrane and into the receiver;

providing a first external force by generating at least one osmotic force to enhance the extraction of the at least one analyte;

analyzing the at least one analyte; and providing the results of the step of analyzing the at least one analyte;

wherein the step of generating at least one osmotic force to enhance the extraction of the at least one analyte comprises:

regulating the at least one osmotic force with a second external force selected from the group consisting of heat, a temperature force, a pressure force, an electromotive force, mechanical agitation, ultrasound, iontophoresis, an electromagnetic force, a magnetic force, a photothermal force, a photoacoustic force, and combinations thereof.

19. A method for non-invasive body fluid sampling and analysis, comprising:

identifying an area of biological membrane having a permeability level;

increasing the permeability level of the area of biological membrane;

contacting the area of biological membrane with a receiver;

extracting at least one analyte of the body fluid through and out of the area of biological membrane and into the receiver;

providing a first external force by generating at least one osmotic force to enhance the extraction of the at least one analyte;

analyzing the at least one analyte; and providing the results of the step of analyzing the at least one analyte; wherein the step of generating at least one osmotic force to enhance the extraction of the at least one analyte comprises:

manipulating at least one of an intensity of the at least one osmotic force, a duration of the at least one osmotic force, and a frequency of the at least one osmotic force with a second external force.

20. The method of claim 19, wherein the second external force is generated by a method selected from the group consisting of: applying an electric field force, applying a magnetic field force; applying an electromagnetic field force; applying a chemical;

adjusting a molarity of the at least one osmotic agent; adjusting a pH level of the at least one osmotic agent; applying an ultrasonic field force; applying an electroosmotic field force;

applying a iontophoretic field force; applying an electroporatic field force; and combinations thereof.

21. A method for non-invasive body fluid samling and analysis, comprising:

identifying an area of biological membrane having a permeability level;

increasing the permeability level of the area of biological membrane;

contacting the area of biological membrane with a receiver;

extracting at least one analyte of the body fluid through and out of the area of biological membrane and into the receiver;

providing an external force to enhance the extraction of the at least one analyte;

analyzing the at least one analyte; and providing the results of the step of analyzing the at least one analyte;

wherein the step of analyzing the at least one analyte comprises:

determining an analyte flux for the at least one analyte from the body fluid based on an analyte flux for a plurality of analytes from the body fluid.

22. A method for non-invasive body fluid sampling and analysis, comprising:

identifying an area of biological membrane having a permeability level;

increasing the permeability level of the area of biological membrane;

contacting the area of biological membrane with a receiver;

extracting at least one analyte of the body fluid through and out of the area of biological membrane and into the receiver;

providing an external force to enhance the extraction of the at least one analyte;

analyzing the at least one analyte; and providing the results of the step of analyzing the at least one analyte; and removing the receiver from the area of biological membrane after a predetermined condition.

23. The method of claim 22, wherein the step of removing the receiver from the area of biological membrane after a predetermined condition comprises:

removing the receiver from the area of biological membrane after an amount of the at least one analyte sufficient for analysis is received in the receiver.

24. The method of claim 23, wherein the step of removing the receiver from the area of biological membrane after a predetermined condition comprises:

removing the receiver from the area of biological membrane within 15 minutes after the receiver contacts the area of biological membrane.

25. The method of claim 23, wherein the step of removing the receiver from the area of biological membrane after a predetermined condition comprises:

removing the receiver from the area of biological membrane within 10 minutes after the receiver contacts the area of biological membrane.

26. The method of claim 23, wherein the step of removing the receiver from the area of biological membrane after a predetermined condition comprises:

removing the receiver from the area of biological membrane within 5 minutes after the receiver contacts the area of biological membrane.

27. A system for non-invasive body fluid sampling and analysis comprising:

a device for measuring a permeability level of an area of biological membrane;

an ultrasonic applicator that applies the ultrasound to the area of biological membrane;

a controller that controls the generation of ultrasound in response to permeability measurements;

a receiver that contacts the area of biological membrane and receivers at least one analyte of the body fluid through and out the area of biological membrane, the receiver comprising:

a medium; and a meter that interacts with thge receiver and detects the analyte flux for the at least one analyte entering the receiver.

28. The system of claim 27, further comprising:

a cartridge containing an ultrasonic coupling solution that is inserted into the ultrasound applicator.

29. The system of claim 27, wherein the ultrasonic applicator comprises:

a cartridge chamber that receives the cartridge; and a solution chamber that receives the ultrasonic coupling solution from the cartridge.

30. The system of claim 27, wherein the medium comprises at least one osmotic agent and at least one of a hydrogel layer, a fluid, and a liquid.

31. The system of claim 30, wherein the osmotic agent comprises: at least one of sodium chloride, lactate and magnesium sulfate.

32. The system of claim 31, wherein the medium further comprises: at least one agent.

33. The system of claim 27, wherein the meter comprises:

a processor; and a device that detects the analyte flux selected from the group consisting of: an electrochemical detector; a biochemical detector; a fluorescence detector; a reflectance detector; a Raman detector; a magnetic detector; a mass spectrometryt detector; an IR spectroscopy detector; and combinations thereof.

34. The system of claim 27, wherein the meter comprises a display that displays an analayte flux.

35. The system of claim 27, further comprising:

a device that provides a first additional energy/force to the area of biological membrane.

36. The system of claim 27, further comprising:

a target ring that is attached to the area of biological membrane.

37. The system of claim 36, wherein the target ring is preapplied with an adhesive.

38. The system of claim 29, wherein the meter is wearable.

39. A system for non-invasive body fluid sampling and analysis comprising:

a controller that controls the generation of ultrasound;

an ultrasonic applicator that applies the ultrasound to an area of biological membrane;

a receiver that contracts the area of biological membrane and receives at least one analyte of the body fluid through and out of the area biological membrane, the receiver comprising:

a medium; and a meter that interacts with the receiver and detects analyte flux for the at least one analyte entering the receiver;

a device that provides a first additional energy/force to the area of biological membrane, and a second receiver in communication with the receiver and having a concentration of the at least one analyte;

wherein the concentration of the at least one analyte in the second receiver is maintained at a level that is lover than a concentration of the at least one analyte received in the receiver.

40. The system of claim 39, further comprising:

a device that provides a second additional energy/force to the receiver.

41. The system of claim 40, wherein the first additional energy/force and the second additional energy/force differ in at least one of a type, a duraton, and an intensity.

42. A method for noninvasive body fluid sampling and analysis, comprising:

enhancing a permeability level of an area of biological membrane;

attaching a receiver to the area of biological membrane;

extracting at least one analyte through and out of the area biological membrane;

receiving the at least one analyte in the receiver; and determining a flux of at least one analyte from the body fluid, based on the flux of a plurality of analaytes from the body fluid.

43. The method of claim 42, wherein the step attaching a receiver to the area of biological membrane comprises:

using an adhesive to contact the receiver to the area of biological membrane.

44. The method of claim 42, wherein the step of determining a flux of at least one analyte from the body fluid comprises:

using a method selected from the group consisting of electrochemical, biochemical, optical, fluorescence, absorbance, reflectance, Raman, magnetic, mass spectrometry, IR spectroscopy measurement methods, and combinations thereof to measure the flux of the at least one analyte.

45. The method of claim 42, wherein the step of determining a flux of at least one analyte from the body fluid comprises:

providing a meter to analyze the at least one analyte using a method selected from the group consisting of electrochemical, biochemical, optical, fluorescence, absorbance, reflectance, Raman, magnetic, mass spectrometry, IR spectroscopy measurement methods, and combinations thereof.

46. The method of claim 43, further comprising the step of:

wearing the meter.

47. The method of claim 42, wherein the step of determining a flux of at least one analyte from the body fluid comprises:

continuously determining the flux for at least one analyte from the body fluid.

48. The method of claim 42, wherein the step of determining a flux of at least one analyte from the body fluid comprises:

periodically determining the flux of at least one analyte from the body fluid.

49. The method of claim 42, further comprising:

displaying the flux of the at least one analyte.

50. The method of claim 42, wherein the step of attaching a receiver to the area of biological comprises:

attaching the receiver to the area of biological membrane for at least 24 hours.

51. The method of claim 42, wherein the step of attaching a receiver to the area of biological membrane comprises:

attaching the receiver to the area of biological membrane for at least 12 hours.

52. The method of claim 42, wherein the step of attaching a receiver to the area of biological membrane comprises:

attaching the receiver to the area of biological membrane for at least 6 hours.

53. The method of claim 42, wherein the step of attaching a receiver to the area of biological membrane comprises:

attaching the receiver to the area of biological membrane for at least 2 hours.

54. A device for noninvasive body fluid sampling and analysis, comprising:
- a receiver that is adapted to be attached to an area of biological membrane with an enhanced permeability and adapted to receiver at least one analyte through and out of the area of biological membrane, the receiver comprising:
- a medium; and
- a wearable meter that measures the flux of the at least one analyte in a continuous manner, the wearable meter comprising:
- a processor; and
- a device that detects the flux of the analyte selected from the group consisting of: an electrochemcial detector, a biochemical detector; a fluorescence detector, a absorbance detector, a reflectance detector, a Raman detector; a magnetic detector; a mass spectrometry detector, IR spectroscopy detector; and combinations thereof.

55. The device of claim 54, wherein the medium comprises:
- at least one osmotic agent and at least one of a hydrogel layer, a fluid, and a liquid 56. The device of claim 55, wherein the osmotic agent comprises: at least one of sodium chloride, lactate, and magnesium sulfate.

57. The device of claim 55, wherein the medium further comprises: at least one agent.

58. The device of claim 54, wherein the wearable meter further comprises:
- a display that displays the analyte concentration in body fluid.

59. The device of claim 54, wherein the wearable meter further comprises:
- a display that displays an analyte concentration.

60. A receiver that is adapted to be attached to an area of biological membrane with an enhanced permeability and adapted to receive at least one analyte through and out of the area of biological membrane, the receiver comprising:
- a first grid;
- a medium layer comprising at least one agent;
- a membrane that induces a concentration gradient barrier for the at least one agent;
- a counter grid;
- an oxidase layer;
- a detection layer; and
- a voltage source that provides a potential difference between the first grid and the counter grid;
- wherein the at least one analyte flows out of or through the biological membrane to the detector layer via the first grid, the counter grid, and the oxidase layer.

61. The receiver of claim 60, wherein the medium layer comprises at least one of a hydrogel and a liquid.

62. The receiver of claim 60, wherein the at least one agent comprises an osmotic agent.

63. The receiver of claim 62, wherein the osmotic agent comprises negative and positive charged species.

64. The receiver of claim 63, wherein a concentration of the charged species can be changed with the voltage source.

65. The receiver of claim 61, wherein the oxidase layer comprises:
- at least one catalyst or enzyme that detect at least one analyte.

66. The receiver of claim 60, wherein the detection layer further comprises:
- at least one working electrode; and
- at least one reference electrode;
- wherein the at least one working electrode and the at least one reference electrode allow for the detection of the by-products of the oxidase layer to quantify a concentration of the desired analyte of detection.

67. A method for non-invasive body fluid sampling and analysis, comprising:
- a) identifying an area of biological membrane having a permeability level;
- b) increasing the permeability level of said area by applying low frequency ultrasound;
- c) providing a transport force to said area to extract an analyte from a body fluid through said area into a sensing zone in communication therewith; and
- d) continuously analyzing said analyte in said sensing zone.

68. The method of claim 67, wherein said analyte is glucose.

* * * * *

UNITED STATES PATENT AND TRADEMARK OFFICE
CERTIFICATE OF CORRECTION

| | | |
|---|---|---|
| PATENT NO. | : 7,066,884 B2 | Page 1 of 1 |
| APPLICATION NO. | : 09/979096 | |
| DATED | : June 27, 2006 | |
| INVENTOR(S) | : Linda Custer et al. | |

It is certified that error appears in the above-identified patent and that said Letters Patent is hereby corrected as shown below:

On front page, please insert the following before section [60] under the heading "Related U.S. Application Data" --Continuation-in-part of application No. 09/868,442, filed on July 24, 2001, which is a 371 of PCT/US99/30065, filed on Dec. 17, 1999.--

Item (60) after "March 17, 2000" insert --60/112,953, filed Dec. 18, 1998 which claims benefit of provisional application No. 60/112,953, filed Dec. 18, 1998, provisional application No. 60/142,941, filed on July 12, 1999, provisional application No. 60/142,950, filed on July 12, 1999, provisional application No. 60/142,951, filed on July 12, 1999, and provisional application No. 60/142,975, filed on July 12, 1999. Application No. 09/868,442 is a continuation-in-part of application No. 09/227,623, filed on Jan. 8, 1999, now Pat. No. 6,190,315, which claims benefit of provisional application No 60/070,813, filed on Jan. 8, 1998.--

Signed and Sealed this
Thirteenth Day of March, 2012

David J. Kappos
*Director of the United States Patent and Trademark Office*